(12) United States Patent
Muyari et al.

(10) Patent No.: US 9,125,551 B2
(45) Date of Patent: Sep. 8, 2015

(54) LIFTING CAP

(71) Applicant: OLYMPUS CORPORATION, Tokyo (JP)

(72) Inventors: Yuta Muyari, Tokyo (JP); Keita Suzuki, Tokyo (JP); Tsutomu Okada, Tokyo (JP); Shunsuke Motosugi, Hirosaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/074,189

(22) Filed: Nov. 7, 2013

(65) Prior Publication Data

US 2014/0066707 A1 Mar. 6, 2014

Related U.S. Application Data

(62) Division of application No. 12/016,700, filed on Jan. 18, 2008, now Pat. No. 8,602,970.

(30) Foreign Application Priority Data

Jan. 22, 2007 (JP) ................................. 2007-011356

(51) Int. Cl.
*A61B 1/00* (2006.01)
*A61B 17/00* (2006.01)
(Continued)

(52) U.S. Cl.
CPC ......... *A61B 1/00087* (2013.01); *A61B 1/00089* (2013.01); *A61B 1/00098* (2013.01); *A61B 1/018* (2013.01); *A61B 17/00234* (2013.01); *A61B 17/0218* (2013.01); *A61B 17/0469* (2013.01); *A61B 17/083* (2013.01); *A61B 17/122* (2013.01); *A61B 17/1285* (2013.01); *A61B 17/221* (2013.01); *A61B 17/29* (2013.01);
(Continued)

(58) Field of Classification Search
CPC ............ A61B 1/0008; A61B 1/00087; A61B 1/00089; A61B 1/00098; A61B 1/00101
USPC ................................. 600/106–107, 127, 129
See application file for complete search history.

(56) References Cited

U.S. PATENT DOCUMENTS 4,178,920 A 12/1979 Cawood, Jr. et al.
4,245,624 A 1/1981 Komiya
(Continued)

FOREIGN PATENT DOCUMENTS

DE 1 225 813 9/1966
JP 8117232 A 5/1996
(Continued)

OTHER PUBLICATIONS

Partial European Search Report dated Nov. 8, 2011 issued in corresponding European Application No. 08 00 0981.4.
(Continued)

*Primary Examiner* — Matthew J Kasztejna
(74) *Attorney, Agent, or Firm* — Scully, Scott, Murphy & Presser, PC

(57) ABSTRACT

An endoscope procedure instrument provided with: a tube part that is cylindrical in shape and attaches to the front end of the endoscope, the tube part having a slit provided to the side surface thereof extending along the direction of the central axis; and a grasping member that is disposed to the tube part extending along the slit, for holding a biologic tissue with respect to the endoscope.

10 Claims, 23 Drawing Sheets

(51) Int. Cl.

| | | |
|---|---|---|
| *A61B 17/02* | (2006.01) | |
| *A61B 17/122* | (2006.01) | |
| *A61B 17/128* | (2006.01) | |
| *A61B 17/29* | (2006.01) | |
| *A61B 17/34* | (2006.01) | |
| *A61B 1/018* | (2006.01) | |
| *A61B 17/04* | (2006.01) | |
| *A61B 17/08* | (2006.01) | |
| *A61B 17/221* | (2006.01) | |
| *A61B 18/14* | (2006.01) | |
| *A61B 17/30* | (2006.01) | |
| *A61B 17/32* | (2006.01) | |
| *A61B 19/00* | (2006.01) | |

(52) U.S. Cl.
CPC ......... *A61B 17/3478* (2013.01); *A61B 18/1442* (2013.01); *A61B 2017/00269* (2013.01); *A61B 2017/00296* (2013.01); *A61B 2017/00349* (2013.01); *A61B 2017/306* (2013.01); *A61B 2017/320044* (2013.01); *A61B 2017/320048* (2013.01); *A61B 2018/1495* (2013.01); *A61B 2019/5408* (2013.01)

(56) References Cited

U.S. PATENT DOCUMENTS

| | | | |
|---|---|---|---|
| 4,401,123 A | 8/1983 | Baba | |
| 4,763,662 A | 8/1988 | Yokoi | |
| 6,071,233 A | 6/2000 | Ishikawa et al. | |
| 6,280,415 B1 | 8/2001 | Johnson | |
| 6,358,197 B1 | 3/2002 | Silverman et al. | |
| 6,719,763 B2 | 4/2004 | Chung et al. | |
| 7,566,300 B2 | 7/2009 | Devierre et al. | |
| 7,575,548 B2 * | 8/2009 | Takemoto et al. | 600/104 |
| 8,277,373 B2 | 10/2012 | Maahs et al. | |
| 2001/0018550 A1 | 8/2001 | Boebel et al. | |
| 2001/0049509 A1 | 12/2001 | Sekine et al. | |
| 2001/0053909 A1 | 12/2001 | Nakada et al. | |
| 2003/0036679 A1 | 2/2003 | Kortenbach et al. | |
| 2003/0176766 A1 | 9/2003 | Long et al. | |
| 2003/0176767 A1 | 9/2003 | Long et al. | |
| 2003/0216727 A1 | 11/2003 | Long | |
| 2003/0225312 A1 | 12/2003 | Suzuki et al. | |
| 2004/0147958 A1 | 7/2004 | Lam et al. | |
| 2004/0172018 A1 | 9/2004 | Okada | |
| 2004/0260149 A1 | 12/2004 | Ishibiki | |
| 2005/0096502 A1 | 5/2005 | Khalili | |
| 2005/0131278 A1 | 6/2005 | Dickopp | |
| 2005/0137453 A1 | 6/2005 | Ouchi et al. | |
| 2005/0234296 A1 | 10/2005 | Saadat et al. | |
| 2005/0234297 A1 | 10/2005 | Devierre et al. | |
| 2006/0235271 A1 * | 10/2006 | Carter et al. | 600/107 |
| 2006/0287572 A1 * | 12/2006 | Wimmer | 600/107 |
| 2007/0167680 A1 * | 7/2007 | Miyamoto et al. | 600/106 |

FOREIGN PATENT DOCUMENTS

| | | | |
|---|---|---|---|
| JP | 09253036 A | 9/1997 | |
| JP | 1156753 A | 3/1999 | |
| JP | 2000037348 A | 2/2000 | |
| JP | 2000166936 A | 6/2000 | |
| JP | 2001120568 A | 5/2001 | |
| JP | 200234905 A | 2/2002 | |
| JP | 2002112946 A | 4/2002 | |
| JP | 2003210389 A | 7/2003 | |
| JP | 2003299663 A | 10/2003 | |
| JP | 2004261372 A | 9/2004 | |
| JP | 2005177098 A | 7/2005 | |
| JP | 2006296488 A | 11/2006 | |
| WO | 2004103430 A2 | 12/2004 | |

OTHER PUBLICATIONS

Japanese Notice of Reasons for Rejection dated Jan. 4, 2011 issued in corresponding Application No. 2007-011356 with English language translation.

Japanese Notice of Reasons for Rejection dated May 25, 2010 issued in corresponding Application No. 2007-011356 with English language translation.

Japanese Notice of Reasons for Rejection dated Jan. 8, 2013 issued in corresponding Application No. 2011-201831 with English language translation.

U.S. Non-Final Office Action dated Apr. 30, 2013 issued in related U.S. Appl. No. 12/016,700.

U.S. Non-Final Office Action dated Jun. 21, 2011 issued in related U.S. Appl. No. 12/016,700.

U.S. Final Office Action dated Oct. 31, 2011 issued in related U.S. Appl. No. 12/016,700.

Extended European Search report dated Apr. 16, 2014 from related European Application No. 14 15 7867.4.

* cited by examiner

LIFTING CAP

CROSS-REFERENCE TO RELATED APPLICATIONS

This application is a divisional application of U.S. application Ser. No. 12/016,700 filed Jan. 18, 2008, which claims the benefit of Japanese Patent Application No. 2007-011356, filed Jan. 22, 2007, the entire contents of each of which are incorporated herein by reference.

BACKGROUND OF THE INVENTION

1. Field of the Invention

The present invention relates to an endoscopic procedure instrument (a lifting cap) for endoscopic resection of a diseased site in the digestive tract.

Priority is claimed on Japanese Patent Application No. 2007-011356, filed Jan. 22, 2007, the content of which is incorporated herein by reference.

2. Description of Related Art

Endoscopic mucosal resection (EMR, hereinafter), in which a diseased site is resected endoscopically, is available as a general method for treating disease of the digestive tract. More specifically, the technique of endoscopic submucosal dissection, (ESD, hereinafter), is a method in which a diseased site is resected by incising the mucosa surrounding the diseased site and then separating away the submucosa. This method is known as a reliable endoscopic treatment that enables complete resection of the diseased site.

When performing this type of ESD, a syringe is employed to inject the healthy mucosa surrounding the diseased site with physiologic saline, etc., causing the diseased site to elevate. In this state, an incision is then made between the diseased site and the healthy mucosa using a high frequency incising instrument such as a high frequency blade or snare (see Japanese Patent Application, First Publication No. 2004-261372, for example). In this case, the diseased site is first lifted up to a sufficient position. Then, in order to adequately hold the area to be cut at the boundary between the diseased site and healthy tissue, and to create an appropriate area of resection in the case where the diseased site is a flat or depressed shape, the transparent cap attached to the front end of the endoscope is inserted under the mucosa, and, as the mucosa is being elevated, the submucosa is incised using a high-frequency incising instrument.

SUMMARY OF THE INVENTION

The endoscope procedure instrument according to the present invention is provided with a tube part that is cylindrical in shape and attaches to the front end of the endoscope, this tube part having a slit provided to the side surface thereof extending along the direction of the central axis; and a grasping member that is disposed to the tube part extending along the aforementioned slit, for holding a biologic tissue with respect to the endoscope.

The endoscope procedure instrument according to the present invention is provided with a tube part that is cylindrical in shape and attaches to the front end of an endoscope; a grasping member for holding a biologic tissue with respect to the endoscope; and a transfer member for moving the holding position of the biological tissue into contact with or away from the tube part by moving the grasping member.

In the endoscope procedure instrument according to the present invention, it is preferable that a slit extending along the central axis be provided in the side surface of the tube part, and that the grasping member be disposed within this slit.

In the endoscope procedure instrument according to the present invention, it is preferable that the grasping member be provided extending along the central axis of the tube part, and that the transfer member be provided with a support member that is connected to the tube part, extends along the central axis and through which the grasping member is inserted in a freely advancing and retracting manner.

In the endoscope procedure instrument according to the present invention, it is preferable that the grasping member be provided extending along the central axis of the tube part, and that the transfer member be in contact with the tube part and be able to move the front end side of the grasping member from the disposed position thereof, toward or away from the direction of the normal line of the outer peripheral surface of the tube part.

In the endoscope procedure instrument according to the present invention, it is preferable that the transfer member be provided with a support member at a first position on the base end side of the tube part through which the grasping member is inserted in a freely advancing and retracting manner with respect to the tube part; and a connector that is provided extending along the grasping member, one end of which is pivot supported about a first rotational axis at a second position on the tube part that is farther toward the front end side than the aforementioned first position, and the other end of which is pivot supported about a second rotational axis on the front end side of the grasping member.

In the endoscope procedure instrument according to the present invention, it is preferable that the grasping member be provided extending along the central axis of the tube part, and that the transfer member be provided with a support member at a first position on the base end side of the tube part through which the grasping member is inserted in a freely advancing and retracting manner with respect to the tube part, while at the same time restricting movement of the grasping member in the radial direction; and an inflatable balloon that is provided to a second position on the grasping member or the tube part that is farther toward the front end than the first position.

Further, in the endoscope procedure instrument according to the present invention, it is preferable that the tube part be provided with a tube main body that is positioned with respect to the front end of the endoscope, and a tongue piece that is pivot supported in a freely rotating manner with respect to the tube main body, and that the transfer member be formed extending along the central axis and be provided with an operating member, the front end of which is connected to the tongue piece at a position that is separated from the position of pivot support for the tube main body and the tongue piece.

In the endoscope procedure instrument according to the present invention, it is preferable that the grasping member be provided with a pair of forceps; an operation wire for carrying out opening/closing manipulation of the pair of forceps; and a sheath through which the operation wire can be inserted in a freely advancing or retracting manner.

In the endoscope procedure instrument according to the present invention, it is preferable that the grasping member be provided with a pair of forceps; an operation wire for opening/closing manipulation of the pair of forceps; and a sheath through which the operation wire is inserted in a freely advancing/retracting manner; and that, with the tube part attached to the endoscope, the grasping member be disposed in the slit so as to enable visual confirmation of the opening/closing operation of the pair of forceps via the endoscope.

Further, in the endoscope procedure instrument according to the present invention, the grasping member is preferably provided with a tube member; and a needle that is inserted from the front end of the tube member in a freely projecting or retracting manner.

In the endoscope procedure instrument according to the present invention, it is preferable that the grasping member be provided with a tube member and a suction source that is connected to the tube member.

In the endoscope procedure instrument according to the present invention, it is preferable that the normal line of the front end surface of the tube member be formed so as to incline in and extend along a direction that separates from the central axis of the tube part when progressing in the direction of the front end of the tube part.

Further, in the endoscope procedure instrument according to the present invention, it is preferable to provide the grasping member with an irregular portion, and that this irregular portion being provided to the surface of the tube part.

The endoscope procedure instrument according to the present invention is provided with a procedure instrument that is inserted into the biological tissue along with the endoscope, and which has a front end part for holding the biological tissue; a connector that connects the front end part of the procedure instrument to the front end part of the endoscope in a manner which permits the front end part of the procedure instrument to move closer to or away from the front end part of the endoscope; a first rotational axis that pivot supports the connector and the front end part of the endoscope; and a second rotational axis that pivot supports the connector and the front end part of the procedure instrument.

Further, in the endoscope procedure instrument according to the present invention, it is preferable that the front end part of the endoscope be provided with a tube part that attaches to the front end of the endoscope in a freely attaching and releasing manner, and at which the connector is pivot supported about the first rotational axis.

Further, in the endoscope procedure instrument according to the present invention, it is preferable that the connector revolve with respect to the front end part of the endoscope via advancing/retracting manipulation of the procedure instrument with respect to the endoscope.

In the endoscope procedure instrument according to the present invention, it is preferable that the front end part of the procedure instrument be farthest separated from the endoscope by revolving the connector to a position where the first rotational axis and the second rotational axis are disposed together in the direction where they are perpendicular to the central axis of the endoscope.

In the endoscope procedure instrument according to the present invention, it is preferable to provide the front end part of the procedure instrument with a pair of forceps, and that the pair of forceps be pivot supported by the second rotational axis and be disposed so as to rotate in a freely opening/closing manner about the second rotational axis.

DETAILED DESCRIPTION OF THE INVENTION

First Embodiment

The first preferred embodiment of the present invention will now be explained with reference to FIGS. 1 through 3.

Figure 1:
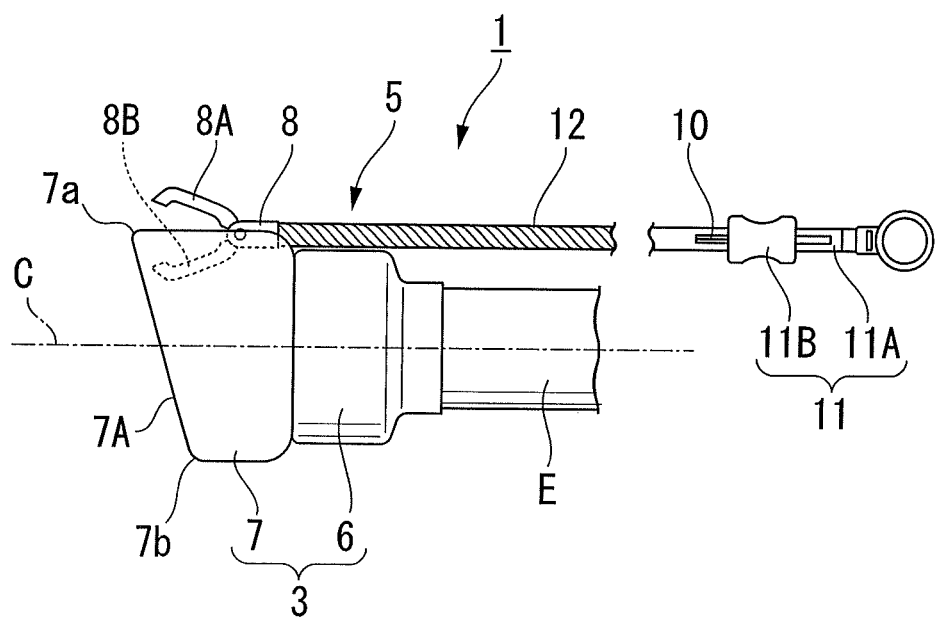
FIG. 1 is a plane view showing the lifting cap according the first embodiment of the present invention.
Figure 2:
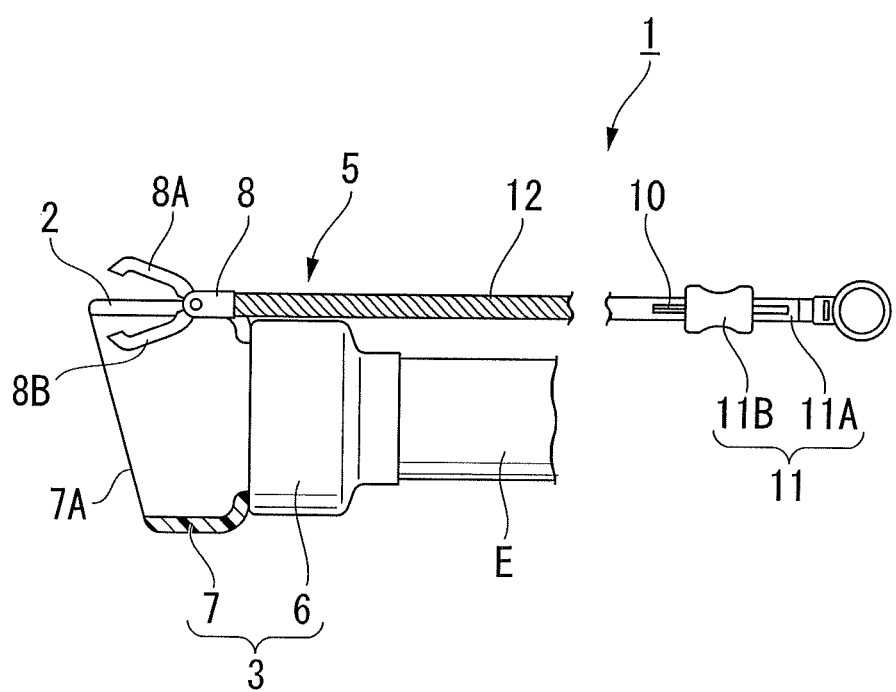
FIG. 2 is a plane view including a partial cross-section showing the lifting cap according to the first embodiment of the present invention.

As shown in FIGS. 1 and 2, a lifting cap (endoscope procedure instrument) 1 according to this embodiment is provided with a tube part 3 that is cylindrical in shape and attaches to the front end of the endoscope E. The tube part 3 has a slit 2 that is formed in its side surface extending along the direction of the central axis C. This lifting cap 1 is further provided with a grasping member 5 that is disposed to the tube part 3 extending along the slit 2 and is for holding a biological tissue relative to the endoscope E.

The tube part 3 is provided with a soft hood 6, the base end of which attaches to the front end of the endoscope E, and a cylindrically shaped, transparent, hard cap 7 which connects to the front end of the hood 6. The front end surface 7A of the cap 7 is inclined with respect to the central axis C of the tube part 3. In other words, this front end surface 7A has a distal point 7a, which is farthest removed from the hood 6, and a proximal point 7b, which is closest to the hood 6. The slit 2 is provided at the distal point 7a on the front end surface 7A of the cap 7.

The grasping member 5 is provided with a pair of forceps 8A,8B that are pivot supported by end cover 8; an operator 11 for performing the opening/closing manipulation of the pair of forceps 8A,8B via an operation wire 10; and a flexible sheath 12 through which the operation wire 10 is inserted in a freely advancing and retracting manner. The sheath 12 is disposed so as to lie along the endoscope E. The operator 11 is provided with an operator main body 11A and a slider 11B that is disposed in a freely advancing and retracting manner with respect to the operator main body 11A. The base end of the sheath 12 is connected to the operator main body 11A, and the base end of the operation wire 10 is connected to the slider 11B.

When the tube part 3 is connected to the end of the endoscope E, the end cover 8 of the grasping member 5 is disposed in the slit 2 of the tube part 3 so that it is as to permit viewing of the opening/closing operation of the pair of forceps 8A,8B via the endoscope E.

Next, the action of the lifting cap 1 according to this embodiment will be explained using as an example the case where performing an ESD procedure employing the aforementioned lifting cap 1.

First, an endoscope E, to the end of which is attached the tube part 3 of the lifting cap 1, is inserted to reach the vicinity of the targeted diseased site X, and a syringe needle, not shown in the figures, is introduced into the abdominal cavity via the endoscope E. Physiologic saline is then injected into the submucosa S of the diseased site X, elevating the diseased site X.

Next, as disclosed in Japanese Patent Application, First Publication No. 2004-261372, a publicity known high-frequency blade, not shown in the figures, is introduced endoscopically and an initial incision is made by opening a hole in the part of the mucosa M surrounding the diseased site X. Next, in this arrangement, the blade, not shown, is advanced while being supplied with a high frequency current, thereby widening the initial opening to a specific size. The cut opening CU formed in the mucosa M near the diseased site X is then brought into contact with a different blade, not shown, and the submucosa S of the diseased site X is cut and separated away.

Next, by bending manipulation of the endoscope E, the position of the cap 7 is adjusted so that the slit 2 of the cap 7 becomes located at the uppermost position of the tube part 3. The position of the tube part 3 is then adjusted while being inclined so as to pass under the cut opening CU. Following positioning, the slider 11B is advanced relative to the operator main body 11A, causing the pair of forceps 8A,8B to open. The cut opening of the mucosa M is thereby interposed between the pair of forceps 8A,8B. In this arrangement, the slider 11B is then retracted back toward the operator main body 11A, causing the pair of forceps 8A,8B to close and thereby grip the mucosa M therebetween.

Figure 3:
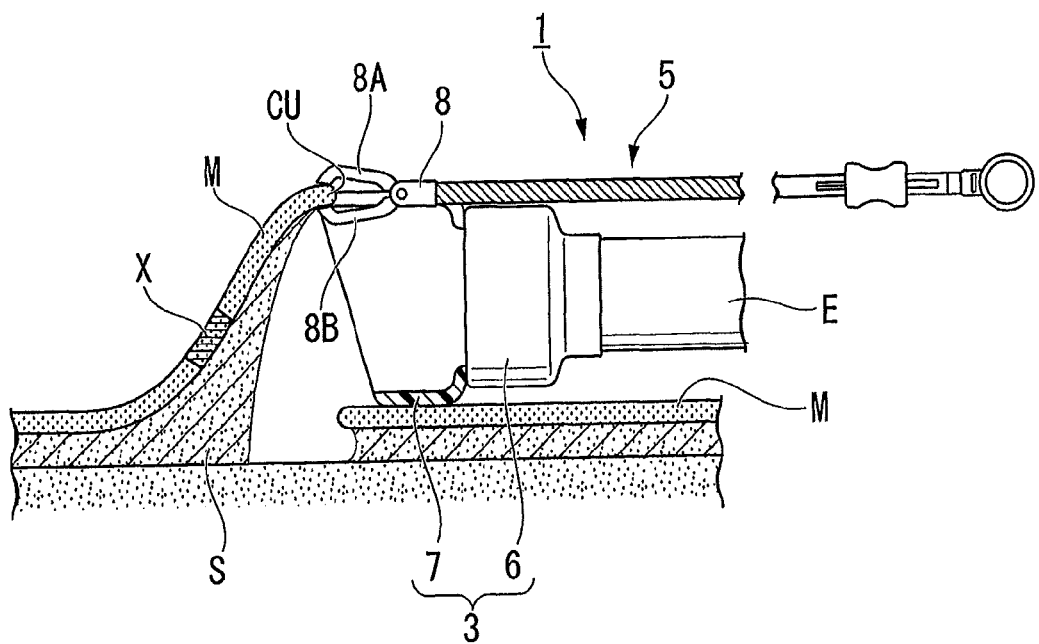
FIG. 3 is a schematic diagram showing the action of the lifting cap according to the first embodiment of the present invention.

Next, as shown in FIG. 3, by positioning the mucosa M on the tube part 3 without changing the relative position of the mucosa M and the tube part 3, the mucosa M is raised up, securing the field of view from the front of the tube part 3. The submucosa S in front of the tube part 3 is then cut and separated away using the blade. Once the incision has been extended to a specific length, the above-describe operation is repeated, so that cutting of the submucosa S progresses as the cut opening CU of the mucosa M is gripped between the pair of forceps 8A,8B.

After the entire diseased site X has been resected, the diseased site X is held with gripping forceps or the like, not shown, and is endoscopically removed, bringing the procedure to a close.

With this lifting cap 1, when incising the submucosa S, in the case where the tube part 3, attached to the endoscope E, has been passed under the mucosa M, the mucosa M is then lifted up with the pair of forceps 8A,8B, and is held so as to permit viewing of the submucosa S from the front via the endoscope E. Further, since the front cover 8 of the grasping member 5 is disposed in the slit 2, it is possible to carry out the procedure while visually confirming the grasping state of the mucosa M by the pair of forceps 8A, 8B from the inner side of the tube part 3 via the endoscope E.

Accordingly, when incising the submucosa S, it is possible to carry out endoscopic operations while continuously maintaining the endoscopic field of view.

In addition, since the grasping member 5 is provided with a pair of forceps 8A,8B, it is possible to grip the biological tissue between the pair of forceps 8A,8B by means of advancing and retracting manipulation of the operation wire 10 with respect to the sheath 12.

Second Embodiment

Next, the second embodiment of the invention will be explained with reference to FIGS. 4 through 6.

Note that compositional elements that are the same as those of the first embodiment will be assigned the same numeric symbol and an explanation thereof will be omitted here.

The point of difference between the first and second embodiments is that, in the second embodiment, the lifting cap 20 is provided with a transfer member 21 for moving the grasping member (procedure tool) 5 so that the holding position of the biological tissue can be moved into contact with or away from the tube part 3.

Figure 4:
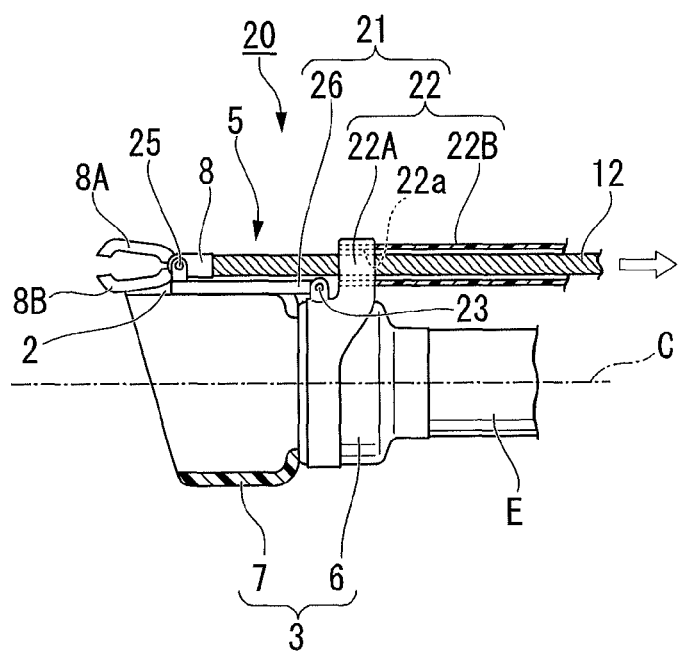
FIG. 4 is a plane view of essential parts showing the lifting cap according to the second embodiment of the present invention.
Figure 5:
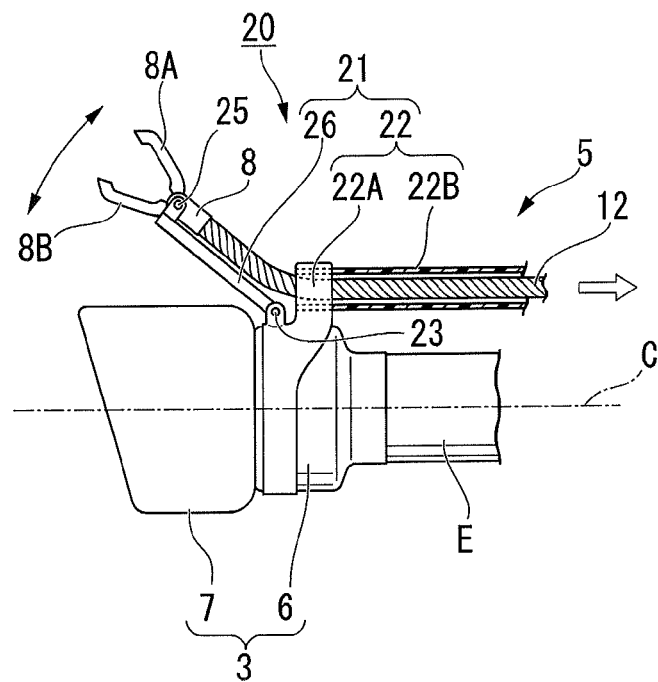
FIG. 5 is a schematic diagram showing the action of the lifting cap according to the second embodiment of the present invention.

As shown in FIGS. 4 and 5, the transfer member 21 is in contact with the tube part 3 and is designed to move the orientation of the front end of the grasping member 5 outward and in the radial direction of the tube part 3. In other words, this transfer member 21 is provided with a support member 22 that is in contact with the hood 6 on the base end of the tube part 3 (first position), and through which the sheath 12 of the grasping member 5 can pass in a freely advancing and retracting manner with respect to the tube part 3, this support member 22 at the same time restricting movement in the radial direction of the tube part 3; and a linking member (connector) 26 that is provided extending along the grasping member 5, one end of which is pivot supported via a first rotational axis 23 at a position on the cap 7 of the tube part 3 that is farther forward than the hood 6 (second position), and the other end of which is pivot supported via a second rotational axis 25 that is disposed to the front cover 8 of the grasping member 5.

This linking member 26 is designed so that the pair of forceps (front ends) 8A,8B of the grasping member 5 are farthest separated from the endoscope E when the first rotational axis 23 and the second rotational axis 25 are revolved to positions at which they are both aligned in a direction perpendicular to the central axis C of the endoscope E.

The support member 22 is provided with a ring-shaped support main body 22A which engages with the hood 6, a portion of this support main body 22A projecting out in the radial direction from the hood 6, wherein an insertion hole 22a is formed for permitting insertion of the sheath 12 along the direction of the central axis C; and an externally attached tube 22B, the front end of which is connected to the support main body 22A so as to communicate with the insertion hole 22a. The pair of forceps 8A,8B are pivot supported on the second rotational axis 25 and are disposed so as to rotate about the second rotational axis 25 in a freely opening and closing manner.

Next, the action of this lifting cap 20 according to the present embodiment will be explained while following through an ESD operation in the same manner as in the first embodiment.

First, the tube part 3 of the lifting cap 20 is attached to the front end of the endoscope E with the linking member 26 positioned so as to lie along the central axis C, and is inserted to the vicinity of the targeted diseased site X, and the diseased site X is elevated.

An initial incision to form an opening in the part of the mucosa M surrounding the diseased site X is made, and a blade, not shown, is then advanced while being supplied with high frequency current. The initial opening is widened to a specific size. In this way, the cut opening CU formed in the mucosa M near the diseased site X is brought into contact with a different blade, not shown, and the submucosa S of the diseased site X is cut and separated away.

At this time, the pair of forceps 8A, 8B are opened and the cut opening CU of the mucosa M is positioned between the pair of forceps 8A, 8B. The slider 11B is then retracted toward the operator main body 11A, causing the pair of forceps 8A, 8B to close and thereby grip the mucosa M therebetween. Then, as in the case of the first embodiment, the mucosa M is positioned with respect to the tube part 3, and the submucosa S in front of the tube part 3 is cut and separated away using the blade.

Once a specific length of submucosa S has been cut, the sheath 12 is pulled toward the proximal side as the cut opening CU of the mucosa M continues to be gripped by the pair of forceps 8A,8B. As the sheath 12 moves toward the base end side, the axial tension imparted on the front cover 8 generates a rotational torque that causes the linking member 26 to rotate around the first rotational axis 23. In this case, because the sheath 12 is flexible, the linking member 26 rotates around the first rotational axis 23, moving the front end of the grasping member 5 away from the tube part 3.

Figure 6:
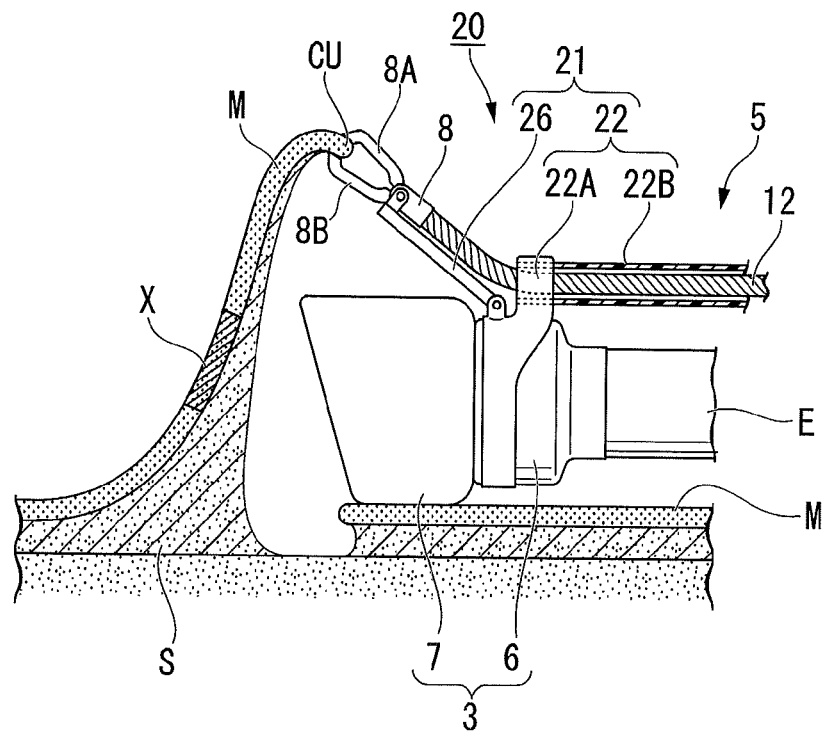
FIG. 6 is a schematic diagram showing the action of the lifting cap according to the second embodiment of the present invention.

Next, as shown in FIG. 6, it is possible to position the mucosa M with respect to the tube part 3, even if the mucosa M is gripped at a position that is distant from the tube part 3. The field of view from the front of the tube part 3 is sufficiently maintained at this time, and the submucosa S in front of the tube part 3 is cut and separated away using the blade.

Once the entire diseased site X has been resected, the diseased site X is held with gripping forceps or the like, not shown, and is endoscopically removed, bringing the procedure to a close.

This lifting cap 20 is provided with not only a grasping member 5, but also a transfer member 21. As a result, even as cutting progresses, it is possible to use this transfer member 21 to move the grasping member 5 to a position that facilitates the procedure and permits a sufficient field of view, while continuing to grip the mucosa M with the grasping member 5. Accordingly, regripping by the grasping member 5 is not necessary, even as cutting progresses. Thus, the procedure can be carried out more easily. Further, it is possible to apply suitable tension on the submucosa S as cutting progresses, making cutting easier.

Third Embodiment

Next, the third embodiment of the present invention will be explained with reference to FIGS. 7 through 10.

Note that compositional elements that are the same as those of the other embodiments will be assigned the same numeric symbol and an explanation thereof will be omitted here.

The point of difference between the second and third embodiments is that, in the third embodiment, the transfer member 31 of the lifting cap 30 according to the third embodiment is further provided with a front end support 32 that can move the grasping member 5 along the direction of the central axis C of the tube part 3.

Figure 7:
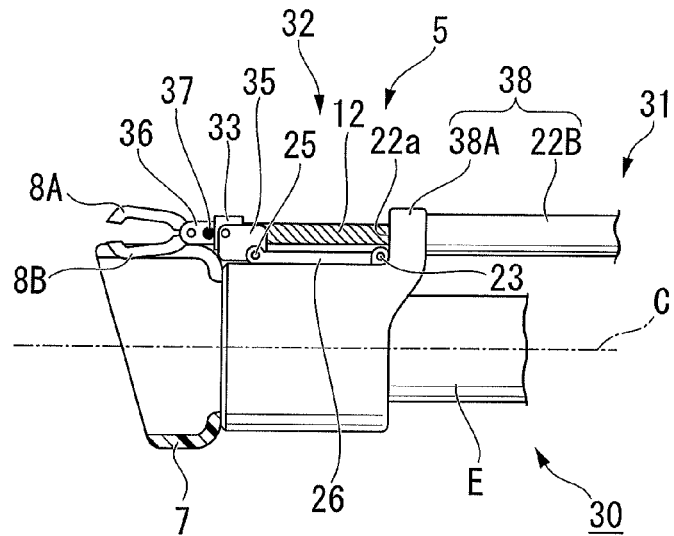
FIG. 7 is a plane view of essential parts showing the lifting cap according to the third embodiment of the present invention.
Figure 8:
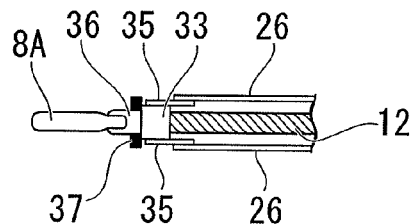
FIG. 8 is a side view of essential parts showing the lifting cap according to the third embodiment of the present invention.

As shown in FIGS. 7 and 8, this front end support 32 is provided with a short tube member 33, through which the sheath 12 can pass in a freely advancing and retracting manner; a front end linking member 35 which is pivot supported by the short tube member 33 via a third rotational axis 34 and is pivot supported by the linking member 26 via the second rotational axis 25; and an end pin 37 that is provided passing through a front end cover 36 in a direction that is perpendicular to the opening/closing plane formed by the pair of forceps 8A,8B. The length of the end pin 37 is greater than the outer diameter of the short tube member 33, and is disposed so as to project outward from the front end cover 36.

A support main body 38A of a support member 38 is formed in the shape of a tube having a sufficient length so that the position of the insertion hole 22a can be separated from the base end of the cap 7 by just the length of the linking member 26.

Next, the action of the lifting cap 30 according to the present embodiment will be explained while following through an ESD operation in the same manner as in the first embodiment.

Figure 9:
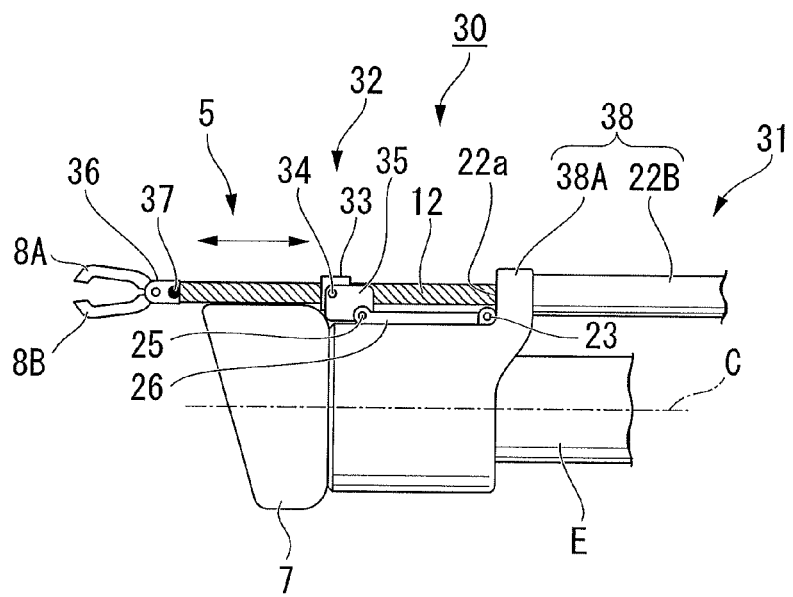
FIG. 9 is a schematic diagram showing the action of the lifting cap according to the third embodiment of the present invention.

As shown in FIG. 9, when cutting and separating away the submucosa of the diseased site, the sheath 12 of the grasping member 5 is advanced to project out the pair of forceps 8A,8B at the front end beyond the tube part 3. In this arrangement, while slightly inclining the tube part 3 at a position removed from the opening, the pair of forceps 8A,8B are opened so that the cut opening of the mucosa is interposed therebetween by means of the same operation as in the second embodiment. The slider 11B is then retracted toward the operator main body 11A, causing the pair of forceps pieces 8A,8B to close and thereby grip the mucosa. Then, as in the case of the second embodiment, the mucosa is positioned on the tube part 3, and the submucosa in front of the tube part 3 is cut and separated away using the blade.

In order to maintain the visual field of the endoscope E once the submucosa has been cut to a specific length, the endoscope E is advanced forward using the sheath 12 as a guide, while the cut opening of the mucosa continues to be gripped by the pair of forceps 8A,8B. At this time, the sheath 12 is relatively moved toward the proximal side until the end pin 37 comes into contact with the short tube member 33.

Figure 10:
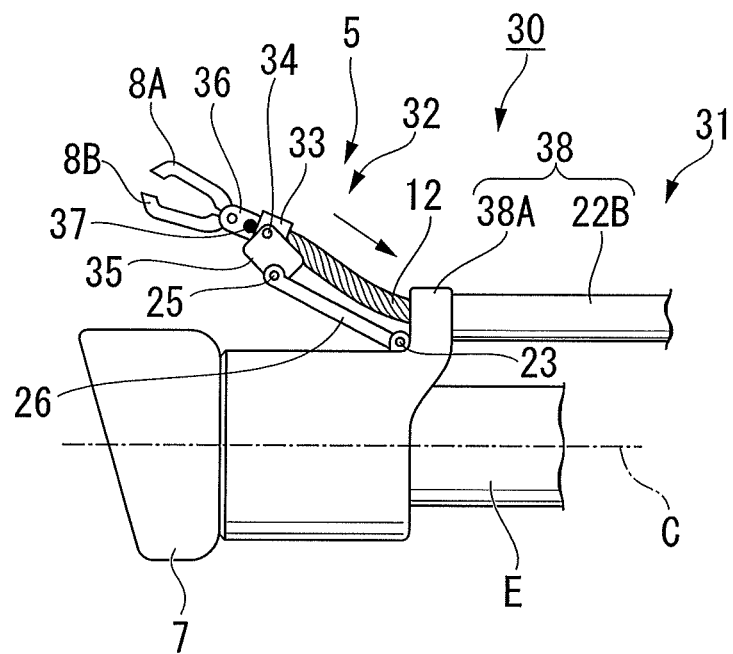
FIG. 10 is a schematic diagram showing the action of the lifting cap according to the third embodiment of the present invention.

When advancing the incision further, with the end pin 37 in a state of contact with the short tube member 33, the sheath 12 is pulled farther toward the proximal side. At this time, as shown in FIG. 10, the front end linking member 35 rotates with respect to the short tube member 33 about the third rotational axis 34, and the linking member 26 rotates with respect to the front end linking member 35 about the first rotational axis 23, thereby moving the front end of the grasping member 5 away from the tube part 3.

In this way, as in the case of the second embodiment, it is possible to position the mucosa with respect to the tube part 3 even when the mucosa is being gripped at a position that is distant from the tube part 3. Next, once the entire diseased site is resected, the diseased site is gripped with gripping forceps or the like, not shown, and is endoscopically removed, bringing the procedure to a close.

With this lifting cap 30, it is possible to advance and retract the sheath 12 with respect to the tube part 3 along the central axis C, and to maintain a pulling tension on the cut opening of the mucosa while varying the position of the tube part 3 and the pair of forceps 8A,8B during incising of the submucosa. Accordingly, it is possible to maintain a sufficient endoscopic field of view, thereby permitting the procedure to be carried out more easily.

Figure 11:
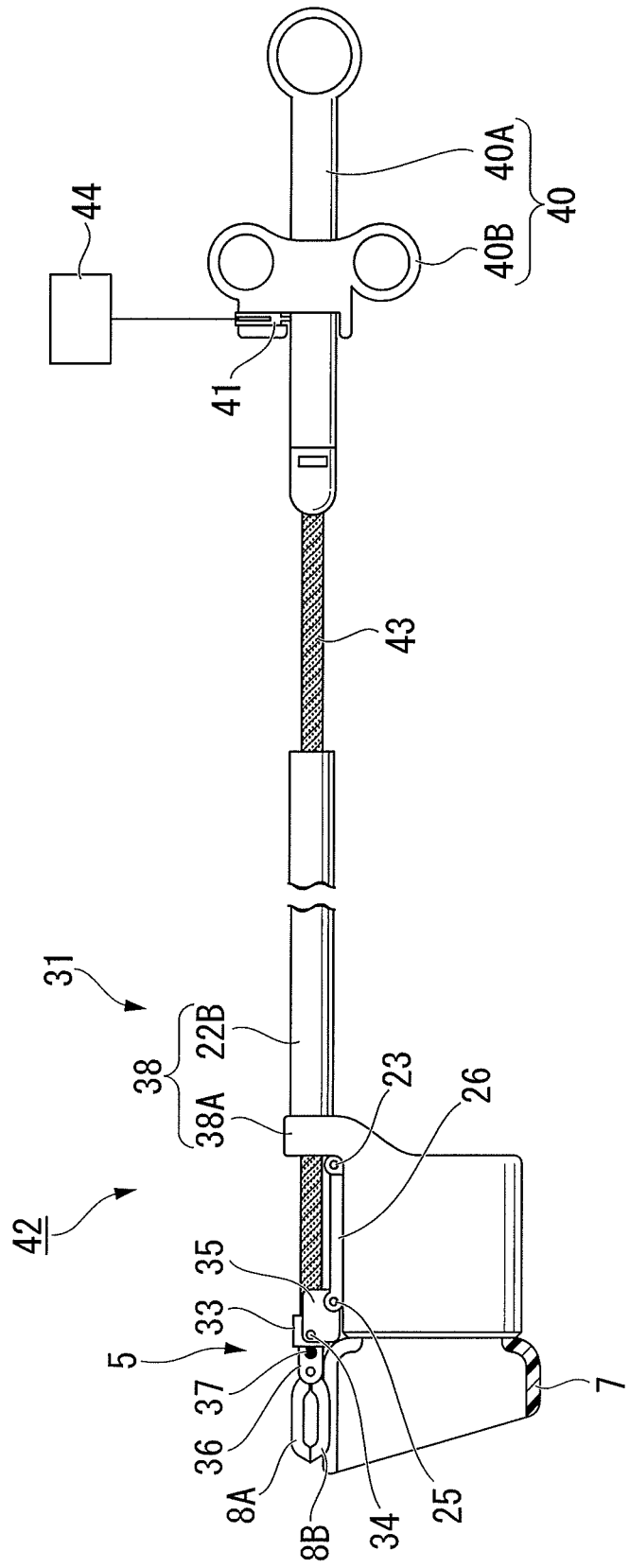
FIG. 11 is a side view showing a modification of the lifting cap according to the third embodiment of the present invention.

Note that as a variation on this embodiment, as shown in FIG. 11, it is also acceptable to employ a lifting cap 42 in which a connecting terminal 41 is provided to a slider 40B that advances and retracts along the operator main body 40A of an operator 40 that is connected to the operation wire 10 of the grasping member 5. In this case, an insulating cover 43 is disposed to the sheath surface.

High frequency current can then be supplied to at least one of the pair of forceps 8A,8B by connecting a high-frequency power source 44 to the connecting terminal 41.

Figure 12:
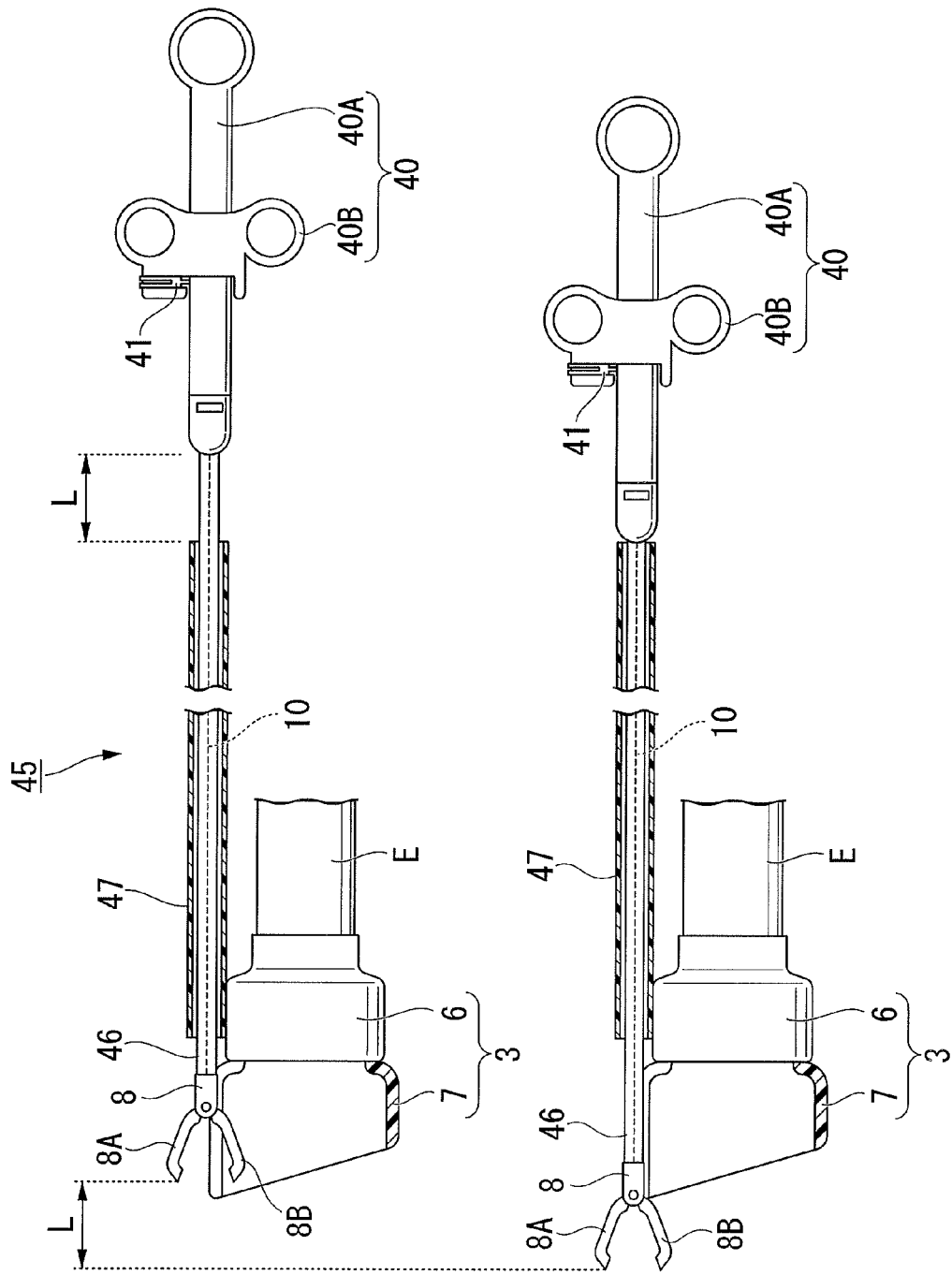
FIG. 12 is a view showing another modification, and the action thereof, of the lifting cap according to the third embodiment of the present invention.

In addition, in the absence of a linking member 26 and the like, as shown in FIG. 12, the outer diameter of the sheath 46 of the lifting cap 45 may be made smaller than the outer diameter of the front cover 8 and the operator main body 40A of the operator 40, and the outer diameter of the externally attached tube 47 may be made larger than the outer diameter of the front cover 8 and the operator main body 40A, and the inner diameter of the externally attached tube 47 may be formed to be smaller than these outer diameters. In this case, the length of the externally attached tube 47 is shorter than the sheath 46 by just a length L. Accordingly, the sheath 46 can be advanced and retracted with respect to the externally attached tube 47 within the limits of this length L, and the pair of forceps 8A,8B can be advanced and retracted by this same length L with respect to the tube part 3.

With this lifting cap 45, as in the case of the lifting cap 1 according to the first embodiment, even if the grasping member 5 cannot move in the radial direction of the tube part 3, it is possible to advance cutting while maintaining continuous pulling tension on the mucosa. Accordingly, the procedure can be carried out easily while maintaining an adequate visual field.

Figure 13:
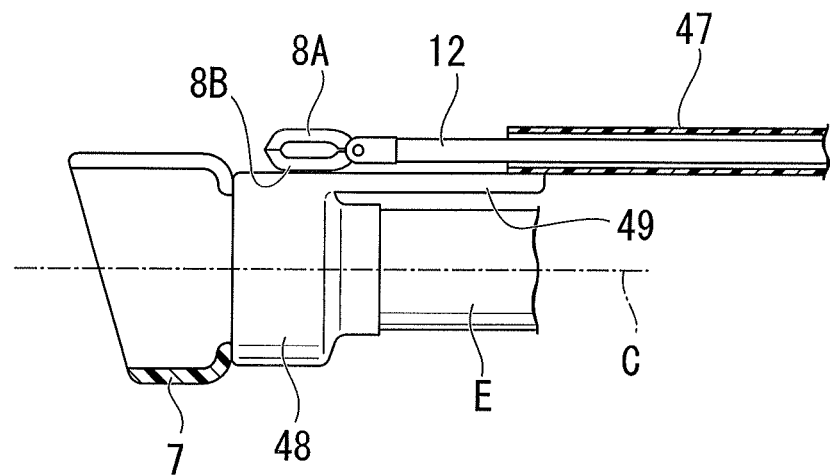
FIG. 13 is a plane view of essential parts showing another modification of the lifting cap according to the third embodiment of the present invention.

Further, as an example of a different modification, as shown in FIG. 13, it is acceptable that an externally attached tube support member 49 be provided extending from the base of a hood 48 toward the proximal side, and that the front end of the externally attached tube 47 be connected to the base end of the externally attached tube support member 49.

In this case, the mucosa can be moved closer to the proximal side than the cap 7 while being gripped by the pair of forceps 8A,8B.

Fourth Embodiment

Next, the fourth embodiment of the invention will be explained with reference to FIGS. 14 through 16.

Note that compositional elements that are the same as those of the other embodiments will be assigned the same numeric symbol and an explanation thereof will be omitted here.

Figure 14:
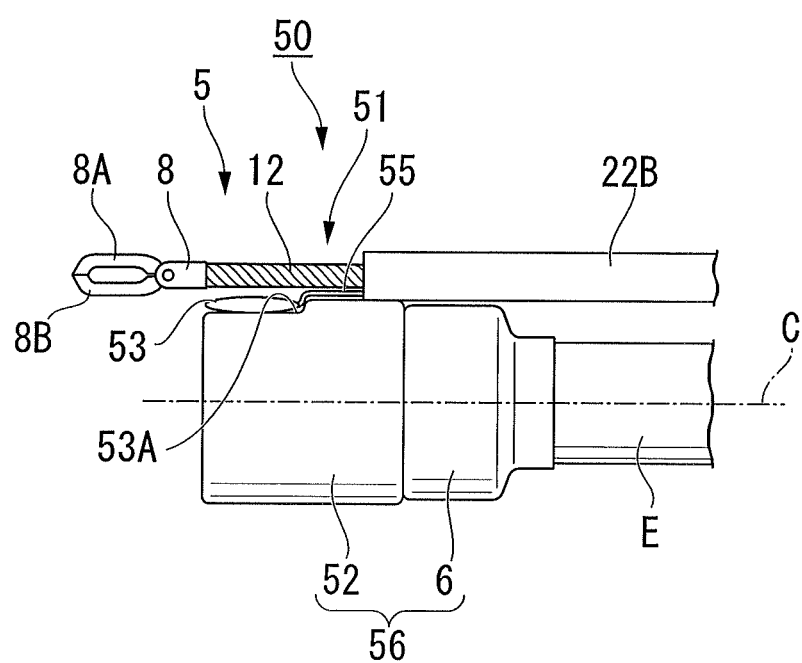
FIG. 14 is a side view of essential parts showing the lifting cap according to the fourth embodiment of the present invention.

The point of difference between the third and fourth embodiments is that, as shown in FIG. 14, the transfer member 51 of the lifting cap 50 according to the fourth embodiment is equipped with an inflatable balloon 53, provided to the side surface of the cap 52, in place of the linking member 26.

This balloon 53 is provided extending over one or both of the cap 52 and the hood 6.

A supplying/evacuating tube 55 is connected to the base end of the balloon 53 for supplying fluid into the balloon and evacuating supplied fluid from the balloon. This supplying/evacuating tube 55 is inserted into the externally attached tube 22B along with the sheath 12, and is connected at its base end to a fluid supply source, not shown in the figures.

A concavity 53A for mounting the balloon 53 is formed in the outer periphery of the cap 52.

Next, the action of the lifting cap 50 according to this embodiment will be explained while following through an ESD operation in the same manner as in the first embodiment.

Figure 15:
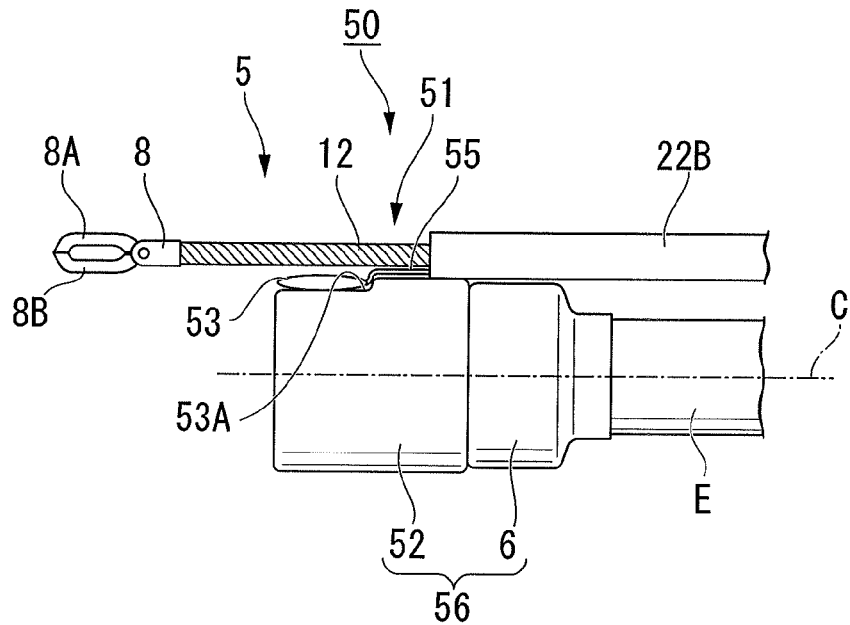
FIG. 15 is a schematic diagram showing the action of the lifting cap according to the fourth embodiment of the present invention.
Figure 16:
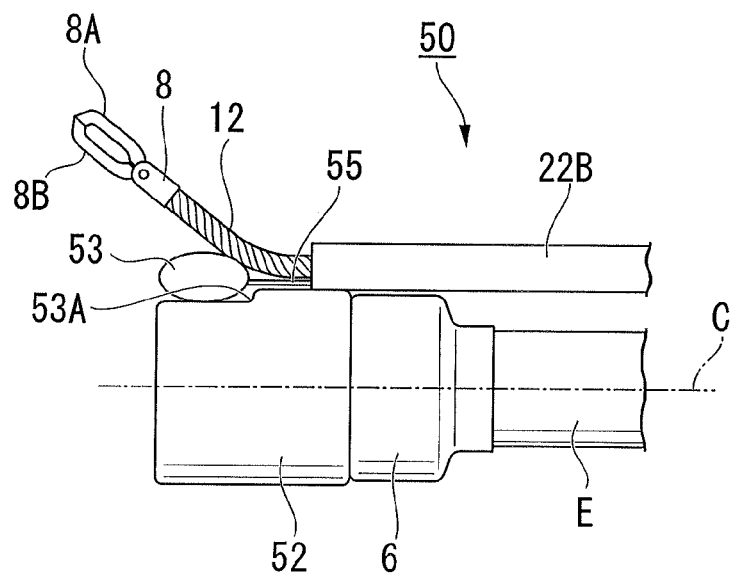
FIG. 16 is a schematic diagram showing the action of the lifting cap according to the fourth embodiment of the present invention.

As shown in FIG. 15, the operations of positioning the mucosa on the tube part 56 after the pair of forceps 8A, 8B have been projected out with respect to the tube part 56, and cutting and separating away the submucosa in front of the tube part 56 using the blade are carried out in the same manner as in the third embodiment.

When further advancing the incision, fluid is supplied from the fluid supply source to the supplying/evacuating tube 55. At this time, as shown in FIG. 16, the balloon 53 expands, so that its diameter widens and pressure is applied on the sheath 12 outward in the radial direction by the balloon 53. In this case, since the balloon 53 is provided to the front end of the externally attached tube 22B, the sheath 12, which is projecting out from the externally attached tube 22B, bends employing the front end of the externally attached tube 22B as a base point. As a result, the front end side of the grasping member 5 moves away from the tube part 56.

As in the case of the second embodiment, it is then possible to position the mucosa with respect to the tube part 56 even if the gripping position of the mucosa is separated from the tube part 56. Next, once the entire diseased site is resected, the diseased site is held with gripping forceps or the like, not shown, and is endoscopically removed, bringing the procedure to a close.

With this lifting cap 50, it is possible to elevate the front end side of the grasping member 5 with respect to the tube part 56 by expanding the balloon 53.

Figure 17:
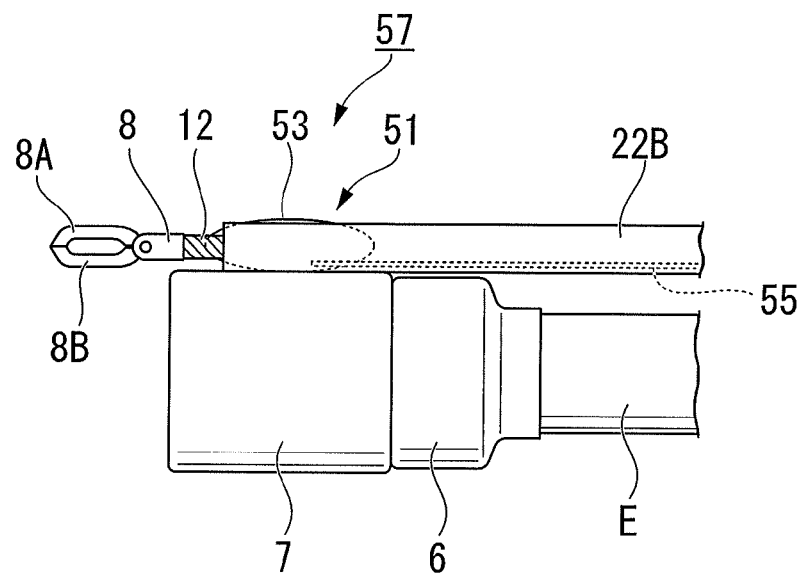
FIG. 17 is a side view of essential parts showing a modification of the lifting cap according to the fourth embodiment of the present invention.
Figure 18:
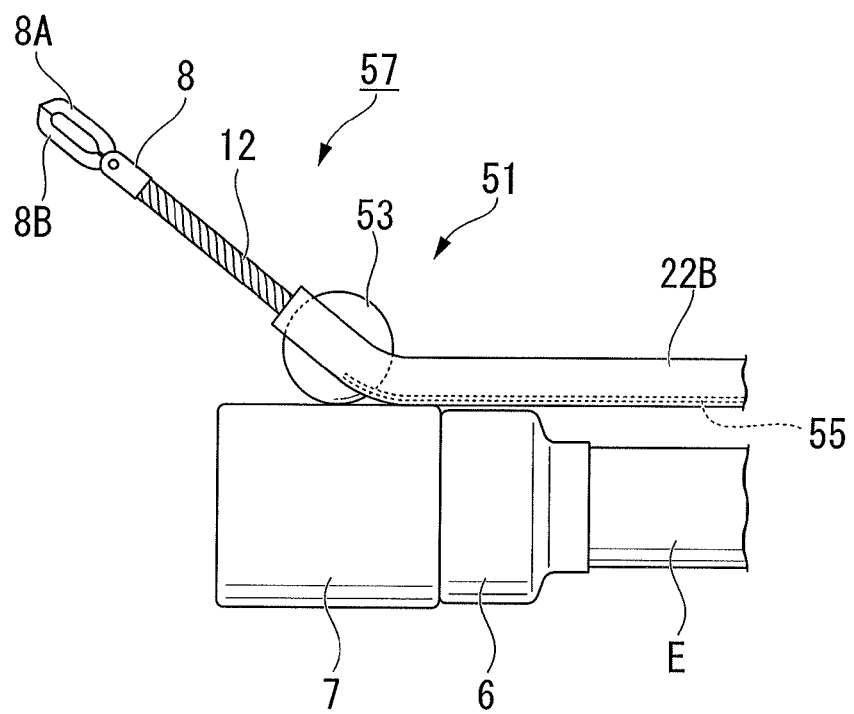
FIG. 18 is a schematic diagram showing the action of a modification of the lifting cap according to the fourth embodiment of the present invention.
Figure 19:
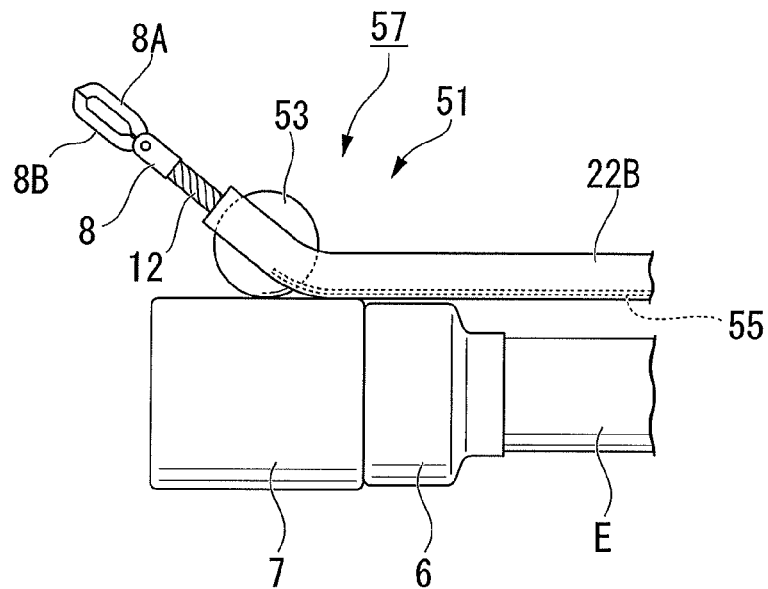
FIG. 19 is a schematic diagram showing the action of a modification of the lifting cap according to the fourth embodiment of the present invention.

Note that as a modification of the present embodiment, it is acceptable to provide a lifting cap 57 in which the balloon 53 is attached to the outer periphery of the externally attached tube 22B, rather than to the cap 52, as shown in FIGS. 17 through 19. In this case, the externally attached tube 22B is disposed so that a specific area from the front end thereof is able to move away from the tube part 56, this portion of externally attached tube 22B having pliability. For this reason, when the balloon 53 is inflated, the front end side of the externally attached tube 22B is elevated in accordance with the widening diameter of the balloon 53, and, accompanying this, the front end side of the grasping member 5 is also raised.

Fifth Embodiment

Figure 20:
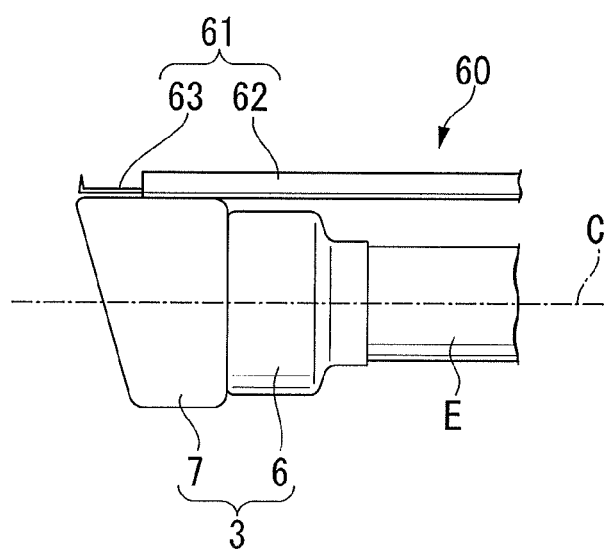
FIG. 20 is a side view of essential parts showing the lifting cap according to the fifth embodiment of the present invention.
Figure 21:
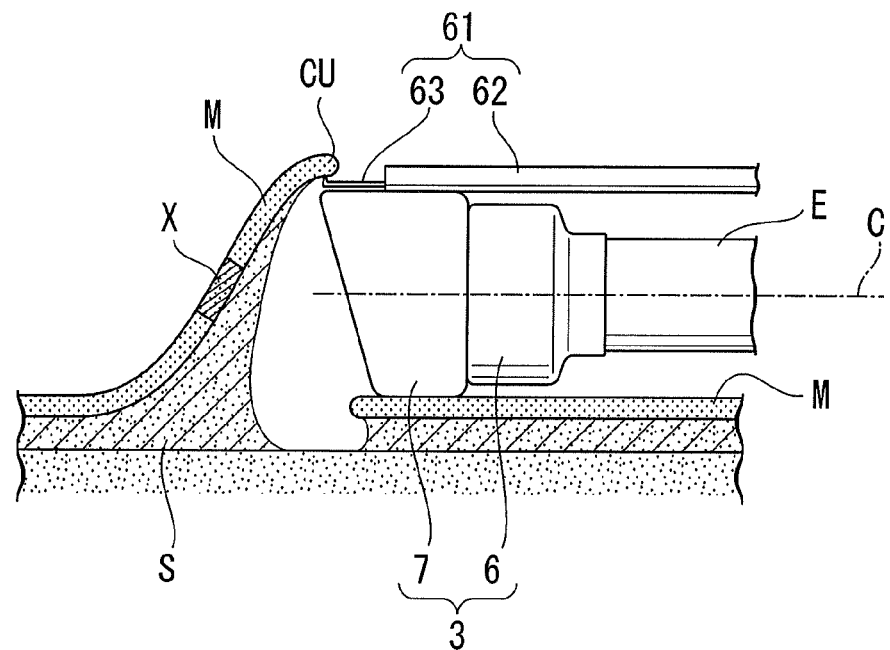
FIG. 21 is a schematic diagram showing the action of the lifting cap according to the fifth embodiment of the present invention.

Next, the fifth embodiment of the invention will be explained with reference to FIGS. 20 and 21.

Note that compositional elements that are the same as those of the other embodiments will be assigned the same numeric symbol and an explanation thereof will be omitted here.

The point of difference between the fifth and first embodiments is that the grasping member 61 of the lifting cap 60 according to this embodiment is provided with an externally attached tube (tube member) 62 and a needle 63 that is inserted in a freely projecting and retracting manner from the front end of the externally attached tube 62.

This needle 63 is connected to the front end of an operation wire, not shown, and is formed so that its front end is curved. The front end of the externally attached tube 62 is connected to the side surface of the cap 7 of the tube part 3.

The action of this lifting cap 60 will be explained while following through an ESD operation in the same manner as in the first embodiment.

First, an endoscope E, to the front end of which is attached the tube part 3 of the lifting cap 60, in which the needle 63 is retracted within the externally attached tube 62, is inserted to the vicinity of the targeted diseased site X, thereby elevating the diseased site X.

Next, an initial incision is made in the same manner as in the first embodiment, and the opening of the initial incision is widened to a specific size. A different blade, not shown, is brought into contact with the cut opening CU formed in the mucosa M near the diseased site X, and the submucosa S of the diseased site X is cut and separated away.

At this time, the needle 63 is projected out to a specific length from the externally attached tube 62, and the cut opening CU of the mucosa M is pierced with the needle 63 by means of a bending manipulation of the endoscope E, thereby gripping the mucosa M. In this way, the mucosa M is positioned with respect to the tube part 3, and the submucosa S in front of the tube part 3 is cut and separated away with the blade.

In order to retain the visual field of the endoscope after incising a specific distance, the endoscope E is advanced forward using the needle 63 as a guide while continuing to pierce the cut opening CU of the mucosa M with the needle 63. At this time, the sheath 12 is moved relatively toward the proximal side until the needle 63 retracts within the externally attached tube 62.

In this way, it is possible to position the mucosa M with respect to the tube part 3 even if the gripping position of the mucosa M is separated from the tube part 3. Next, once the entire diseased site X is resected, the diseased site X is held with gripping forceps or the like, not shown, and is endoscopically removed, bringing the procedure to a close.

With this lifting cap 60, even in the case of a method other than one that relies on opening/closing manipulation of a pair of forceps, it is possible to position the mucosa M with respect to the tube part 3 by projecting a needle 63 from the front end of the externally attached tube 62, and piercing the mucosa M.

Sixth Embodiment

Figure 22:
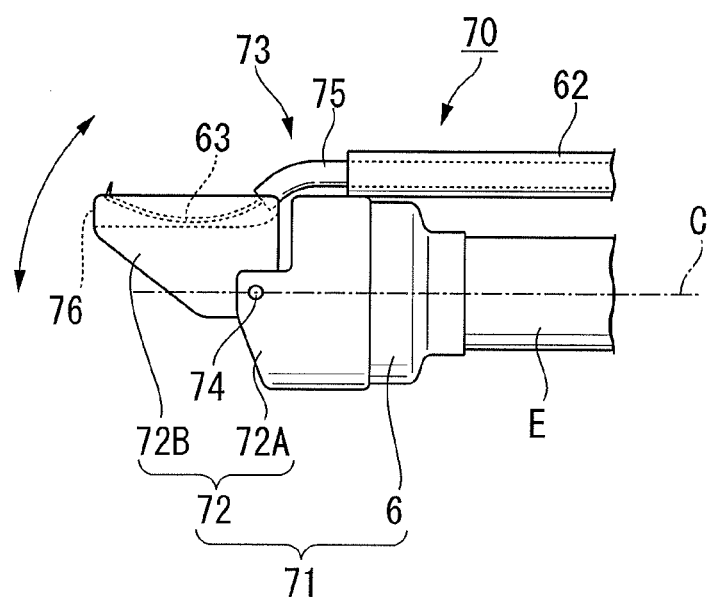
FIG. 22 is a side view of essential parts showing the lifting cap according to the sixth embodiment of the present invention.

Next, the sixth embodiment of the invention will be explained with reference to FIG. 22.

Note that compositional elements that are the same as those of the other embodiments will be assigned the same numeric symbol and an explanation thereof will be omitted here.

The point of difference between the sixth and fifth embodiments is that the cap 72 of the tube part 71 of the lifting cap 70 according to this embodiment is provided with a cap main body (tube main body) 72A that is connected to the hood 6, and a tongue piece 72B that is in the shape of a roughly semicircular cylinder, the tongue piece 72B being pivot supported in a freely rotating manner with respect to the cap main body 72A.

A transfer member 73 is formed extending along the central axis C, and is provided with an operating member 75 that is connected at a specific position on the tongue piece 72B that is separated from a pivot support position 74 for the cap main body 72A and the tongue piece 72B. This operating member 75 is inserted in a freely advancing/retracting manner into the externally attached tube 62 which is connected to the outer periphery of the cap main body 72A in the same manner as the operation wire, not shown in the figures. A slit 76, in which the needle 63 can advance and retract, is provided in the side surface of the tongue piece 72B.

Next, the operation of the lifting cap 70 according to the present embodiment will be explained while following through an ESD operation in the same manner as in the fifth embodiment.

First, as in the case of the fifth embodiment, an endoscope E, to the front end of which is attached a tube part 71 of a lifting cap 70, in which the needle 63 is retracted within the externally attached tube 62, is inserted to the vicinity of the targeted diseased site, thereby elevating the diseased site.

Next, an initial incision is made in the same manner as in the first embodiment, and the opening of this initial incision is widened to a specific size. A different blade, not shown in the figures, is then brought into contact with the cut opening formed in the mucosa near the diseased site, and the submucosa of the diseased site is cut and separated away.

At this time, with the needle 63 retracted within the externally attached tube 62, the tube part 71 is inserted into the cut opening of the mucosa as the tongue piece 72B is rotated and moved with respect to the cap main body 72A by advancing/retracting manipulation of the operating member 75.

With the tongue piece 72B inserted, the needle 63 is projected out by a specific length from the externally attached tube 62, and the cut opening of the mucosa is pierced with the needle 63, thereby gripping the mucosa. The mucosa is thereby positioned with respect to the tube part 71, and cutting and separating away of the submucosa in front of the tube part 71 with the blade is carried out.

Subsequently, as in the case of the fifth embodiment, while continuing to pierce the cut opening of the mucosa with the needle 63 accompanying with the incision, and the endoscope E is advanced forward using the needle 63 as a guide. Once the diseased site has been completely resected, the diseased site is gripped with gripping forceps or the like, not shown, and is removed endoscopically, bringing the procedure to a close.

In this lifting cap 70, the tongue piece 72B of the tube part 71 is pivot supported with respect to the cap main body 72A. As a result, when inserting the tube part 71 into the cut opening of the mucosa, it is possible to insert the tube part 71 while rotating the tongue piece 72B by advancing/retracting manipulation of the operating member 75. Accordingly, it is not necessary to rely on bending manipulation of the endoscope E, and it is possible to proceed with the procedure while keeping the field of view of the endoscope E fixed on the diseased site.

Seventh Embodiment

Figure 23:
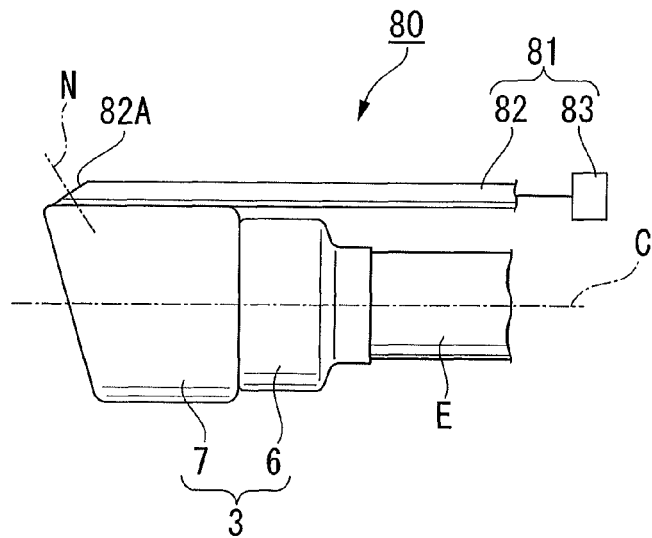
FIG. 23 is a side view of essential parts showing the lifting cap according to the seventh embodiment of the present invention.
Figure 24:
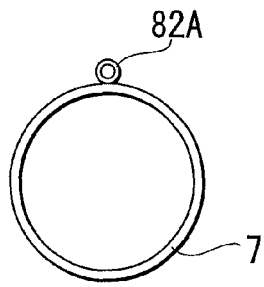
FIG. 24 is a plane view showing the lifting cap according to the seventh embodiment of the present invention.
Figure 25:
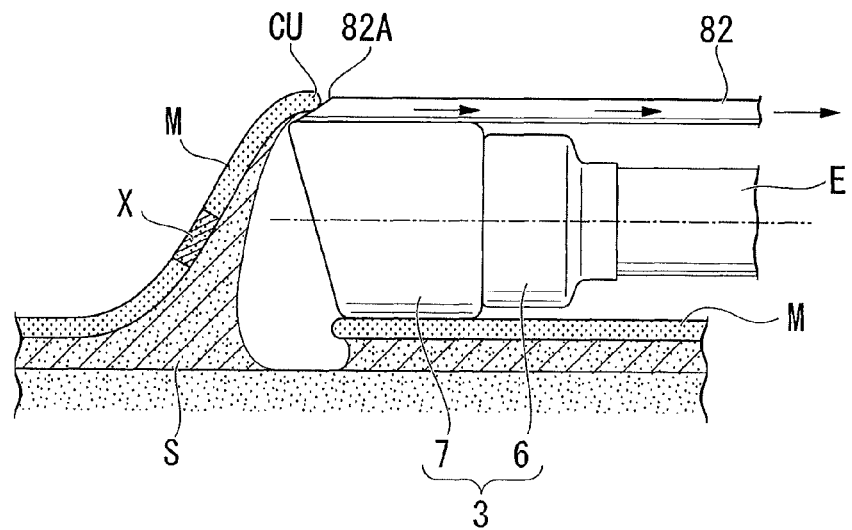
FIG. 25 is a schematic diagram showing the action of the lifting cap according to the seventh embodiment of the present invention.

Next, a seventh embodiment of the invention will be explained with reference to FIGS. 23 through 25.

Note that compositional elements that are the same as those of the other embodiments will be assigned the same numeric symbol and an explanation thereof will be omitted here.

The point of difference between the seventh and first embodiments is that the grasping member 81 of the lifting cap 80 according to the present embodiment is provided with a tube member 82 and a suction source 83 that is connected to the tube member 82.

The front end side of the tube member 82 is disposed in the slit 2 that is provided in the side surface of the tube part 3.

The normal line N of the front end surface 82A of the tube member 82 is formed so as to incline in and extend along a direction that moves away from the central axis C of the tube part 3 when progressing in the direction of the front end of the tube part 3.

Next, the operation of the lifting cap 80 according to the present embodiment will be explained while following through an ESD operation in the same manner as in the first embodiment.

First, an endoscope E, to the front end of which is attached the tube part 3 of the lifting cap 80, is inserted to the vicinity of the targeted diseased site X, and the diseased site X is elevated.

Next, an initial incision is made in the same manner as in the first embodiment, and the opening of this initial incision is widened to a specific size. A different blade, not shown in the figures, is then brought into contact with the cut opening formed in the mucosa M near the diseased site X, and the submucosa S of the diseased site X is cut and separated away.

At this time, the suction source 83 is activated to provide suction, while bringing the cut opening CU of the mucosa M into contact with the front end surface 82A of the tube member 82 by bending manipulation of the endoscope E. The cut opening CU of the mucosa M is gripped at the front end surface 82A of the tube member 82 under the force of the suction. In this way, the mucosa M is positioned with respect to the tube part 3, and the cutting and separating away of the submucosa S in front of the tube part 3 is carried out using the blade.

Once the incision has been extended to a specific length, the above-described process is repeated, so that the incising of the submucosa S progresses while continuing to suction the cut opening CU of the mucosa M.

Once the diseased site X has been completely resected, the diseased site X is gripped with gripping forceps or the like, not shown, and is removed endoscopically, bringing the procedure to a close.

In this lifting cap 80, the tube member 82 is suctioned using the suction source 83; as a result, the mucosa M can be grasped at the front end surface 82A of the tube member 82 via this suction force. In particular, since the normal line N of the front end surface 82A of the tube member 82 is directed and extends outward in the radial direction of the tube part 3, it is possible to increase the area of contact between the front end surface 82A and the mucosa M even more than in the case where the normal line of the front end surface 82A is parallel with the central axis C. As a result, the mucosa M can be grasped with greater reliability.

Note that as a modification of the present embodiment, it is acceptable to provide a lifting cap in which the cap of the tube part is provided with a cap main body that is connected to the hood, and a tongue piece that is in the shape of a roughly semicircular cylinder, which is pivot supported in a freely rotating manner with respect to the cap main body. In this case, the tube part can be passed under the mucosa while rotating and moving the cap main body in the same manner as in the sixth embodiment, and the same procedures as performed in this embodiment can be carried out.

Eighth Embodiment

Figure 26:
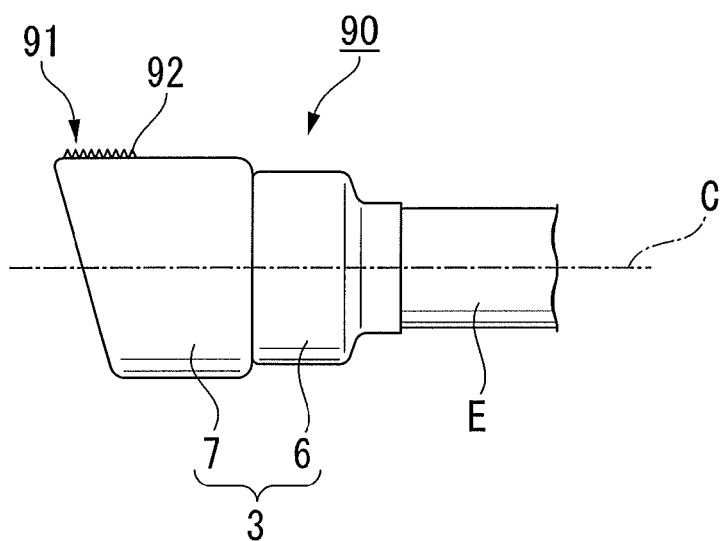
FIG. 26 is a side view of essential parts showing the lifting cap according to the eighth embodiment of the present invention.

Next, an eighth embodiment of the invention will be explained with reference to FIG. 26.

Note that compositional elements that are the same as those of the other embodiments will be assigned the same numeric symbol and an explanation thereof will be omitted here.

The point of difference between the eighth and the first embodiments is that the grasping member 91 of the lifting cap 90 according to the present embodiment is provided with an irregular part 92 that is provided to the surface of the tube part 3.

The irregular part 92 has a coating on its surface so as to make its coefficient of friction greater than that of the other surfaces of the tube part 3. Note that this technique is not limited to coating, but rather, it is also acceptable to change the surface roughness with respect to other components. It is also acceptable to vary the frictional coefficient by providing a brush or the like.

Next, the operation of the lifting cap 90 according to the present embodiment will be explained while following through an ESD operation in the same manner as in the first embodiment.

First, an endoscope E, to the front end of which is attached the tube part 3 of the lifting cap 90, is inserted to the vicinity of the targeted diseased site, an initial incision is made in the same manner as in the first embodiment, and cutting and separating away of the submucosa of the diseased site is carried out.

The tube part 3 is passed under the cut opening while bringing the cut opening of the mucosa into contact with the irregular part 92 of the tube part 3 by bending manipulation of the endoscope E. The frictional force generated between the irregular part 92 and the mucosa is larger than the frictional force generated between other surfaces of the tube part 3 and the mucosa. As a result, the cut opening of the mucosa enters a state of engagement with the irregular part 92. In this way, the mucosa is positioned with respect to the tube part 3, and the submucosa in front of the tube part 3 is cut and separated away using the blade.

Once the incision has been extended to a specific length, the above-described operation is repeated, so that cutting of the submucosa progresses as the cut opening of the mucosa continues to be grasped due to its frictional force with the irregular part 92.

After the diseased site has been completely resected, the diseased site is held with gripping forceps or the like, not shown, and is endoscopically removed, bringing the procedure to a close.

In this lifting cap 90, by bringing the mucosa into contact with the irregular part 92, it is possible to generate a frictional force with the irregular part 92 that is greater than that on other surfaces of tube part 71 which do not have an irregular part 92. As a result, the mucosa can be gripped with respect to the tube part 3.

Figure 27:
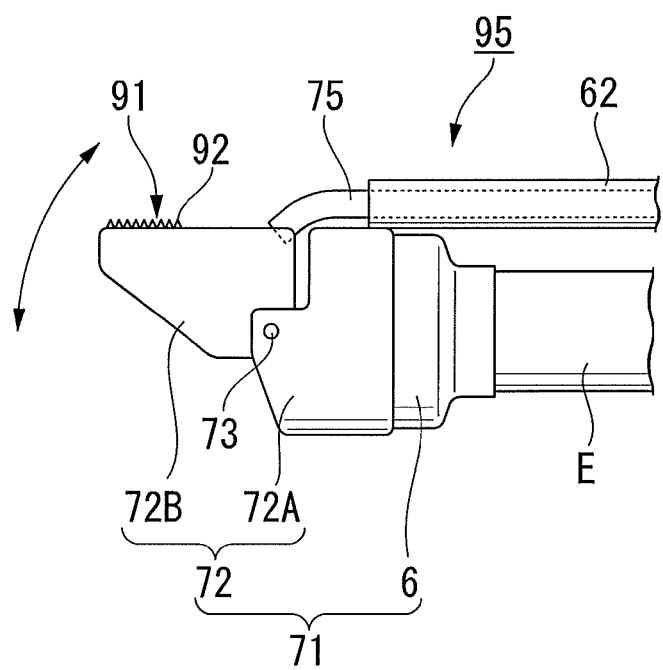
FIG. 27 is a side view of essential parts showing a modification of the lifting cap according to the eighth embodiment of the present invention.

Note that, as shown in FIG. 27, it is also acceptable to provide a lifting cap 95 that has a tube part 71 to which is disposed a cap 72 that is provided with a cap main body 72A that is connected to a hood 6, and a tongue piece 72B that is cylindrical in shape and is pivot supported in a freely rotating manner with respect to the cap main body 72A. In this case, the tube part 3 can be passed under the mucosa while rotating and moving the cap main body 72A in the same manner as in the sixth embodiment, and the same procedures as performed in this embodiment can be carried out.

Figure 28:
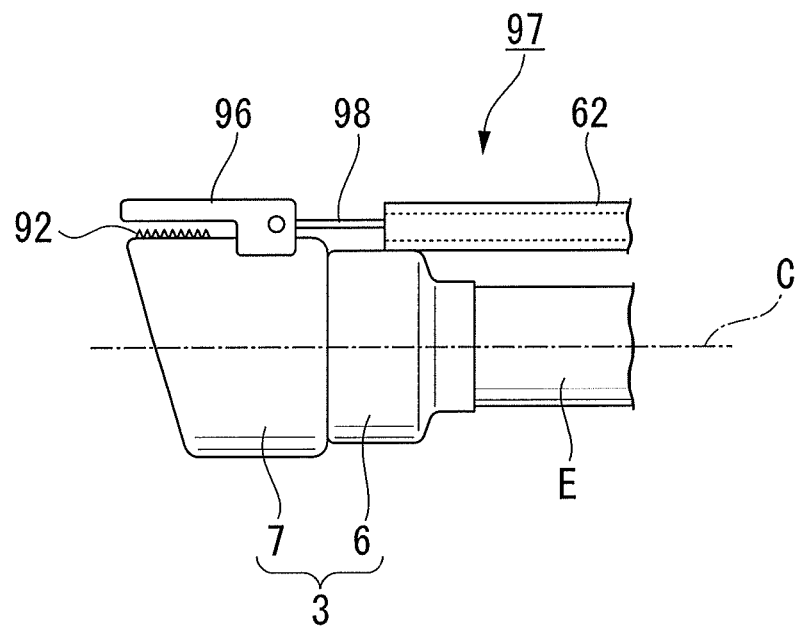
FIG. 28 is a side view of essential parts showing another modification of the lifting cap according to the eighth embodiment of the present invention.
Figure 29:
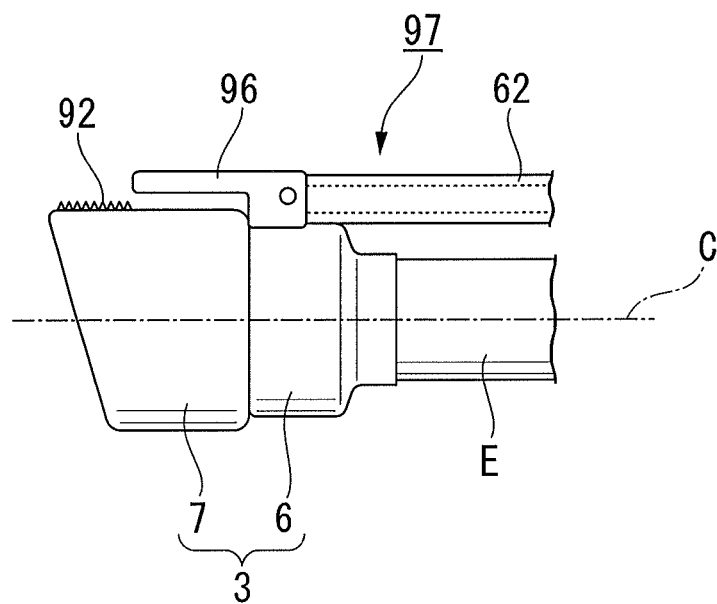
FIG. 29 is a schematic diagram showing the action of the lifting cap shown in FIG. 28.

Further, as a different modification, it is also acceptable to provide a lifting cap 97 that is provided with a cover part 96 for covering the irregular part 92, as shown in FIGS. 28 and 29.

This cover part 96 has the same curvature as the side surface of the tube part 3, and is disposed at a position that is separated from the irregular part 92 by a specific distance in a direction which is outward and radial to the tube part 3. This cover part 96 is connected to an operating member 98 that is inserted in a freely advancing or retracting manner in the externally attached tube 62, the front end of which is connected to the hood 6. Further, cover part 96 is disposed so as to be freely advancing and retracting with respect to the tube part 3. Accordingly, the irregular part 92 can be covered with the cover part 96, or exposed from the cover part 96 through the advancing/retracting manipulation of the operating member 98 with respect to the externally attached tube 62.

Note that the technical scope of the present invention is not limited to the preceding embodiments. Rather, various alterations may be added within a scope which does not depart from the gist of the invention.

Figure 30:
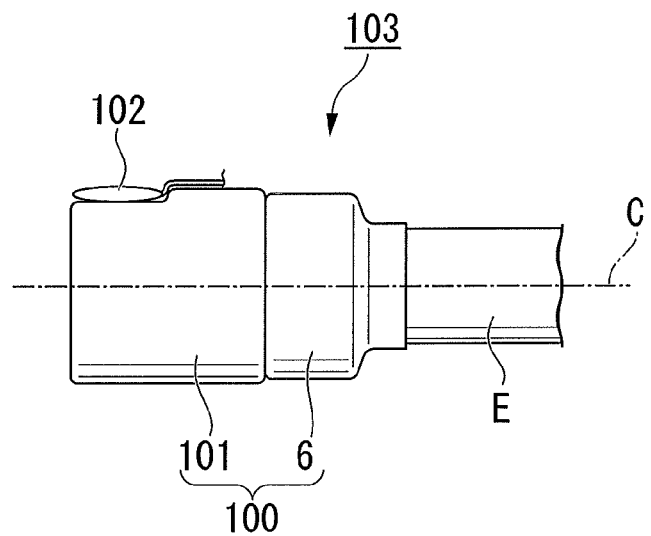
FIG. 30 is a side view of essential parts showing the lifting cap according to another embodiment of the present invention.
Figure 31:
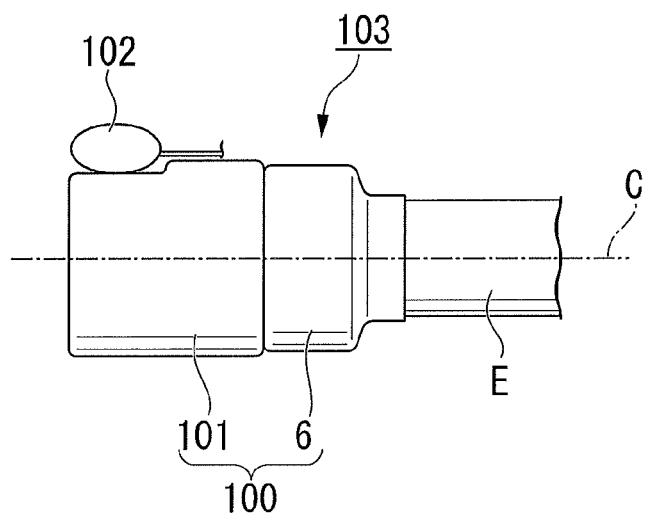
FIG. 31 is a schematic diagram showing the action of the lifting cap shown in FIG. 30.

For example, as shown in FIGS. 30 and 31, a lifting cap 103 may be provided in which the diameter of the balloon 102 which is provided to the cap 101 of the tube part 100 is expanded, so that it comes into direct contact with and lifts the mucosa, not shown in the figure.

Reference examples of other embodiments of the endoscope procedure instrument that is employed in the ESD procedure are shown below.

Figure 32:
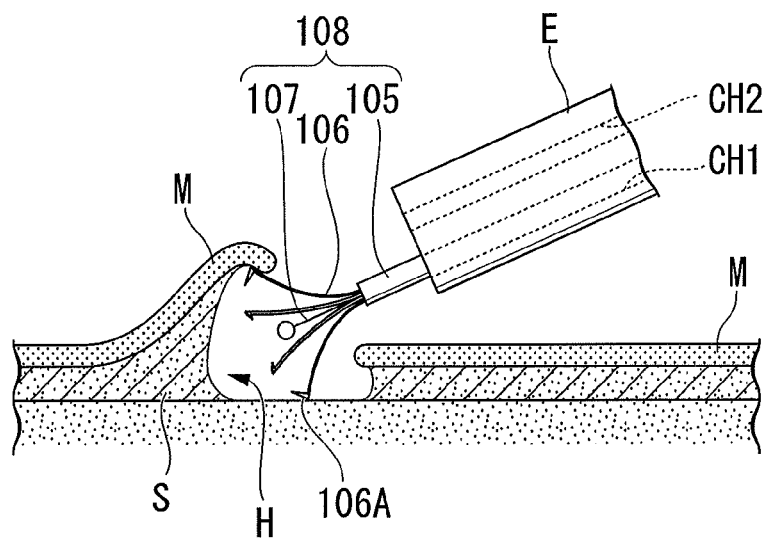
FIG. 32 is a view showing the endoscope procedure instrument, and the action thereof, in accordance with an ESD procedure.

For example, as shown in FIG. 32, it is acceptable to provide a procedure instrument 108 which is provided with a sheath 105; a plurality of legs 106 which are disposed so as to freely retract into and project from the sheath 105; and a blade 107 that is disposed so as to freely retract into and project from the sheath 105. The end of these various legs 106 of the procedure instrument 108 are formed so as to curve in a direction which gradually moves away from the central axis C of the sheath 105. A claw 106A, which curves inward in the radial direction is provided at the front end of the legs 106.

The operation of this procedure instrument 108 will now be explained.

With the legs 106 and the blade 107 retracted within the sheath 105, the sheath 105 is introduced into one of the channels CH1 of an endoscope E which has two instrument insertion channels CH1,CH2. The sheath 105 is projected out from the front end of the channel CH1 of the endoscope E in the direction of a hole H that is formed in the mucosa M, and each of the legs 106 are projected out from the sheath 105.

Since each of the legs 106 is curved, the front ends thereof widen in the direction that is moving away from the central axis C, while at the same time coming into contact with the mucosa M, and lifting up and holding the mucosa M. As a result, the field of view of the endoscope E can be maintained. The blade 107 is then projected out in this state, and, as necessary, a different high-frequency blade, not shown in the figures, is projected out from the other channel CH2, and a specific operation is carried out.

Figure 33:
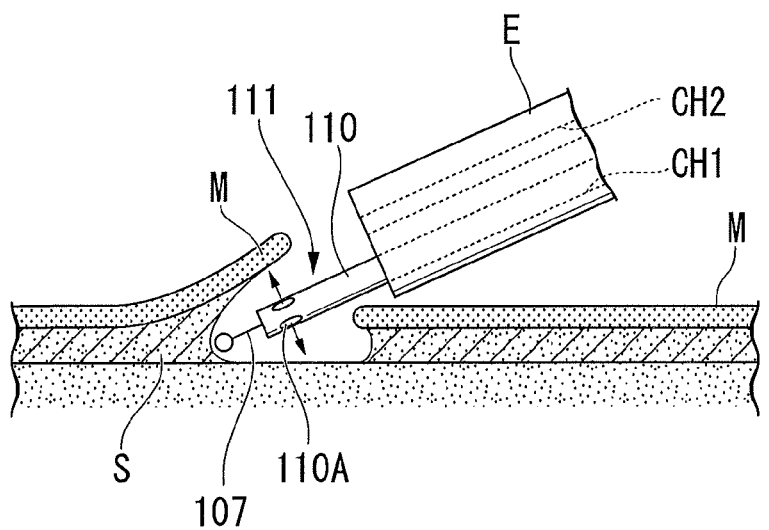
FIG. 33 is a view showing the endoscope procedure instrument, and the action thereof, in accordance with an ESD procedure.

Here, as shown in FIG. 33, it is also acceptable to employ a procedure instrument 108 that has a sheath 105, in which a plurality of delivery holes 110A are provided at the front end in place of the legs 106. This procedure instrument 108 is inserted into the instrument insertion channel CH1, and air or water flow is delivered from a delivery source, not shown in the figures. In this case, it is possible to push up the mucosa M by means of the force generated by the air or water expelled from the delivery holes 110A.

Figure 34:
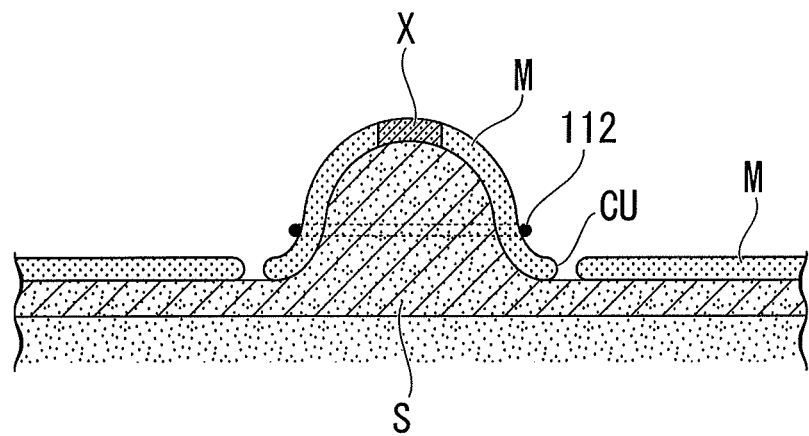
FIG. 34 is a view showing another endoscope procedure instrument, and the action thereof, in accordance with an ESD procedure.
Figure 35:
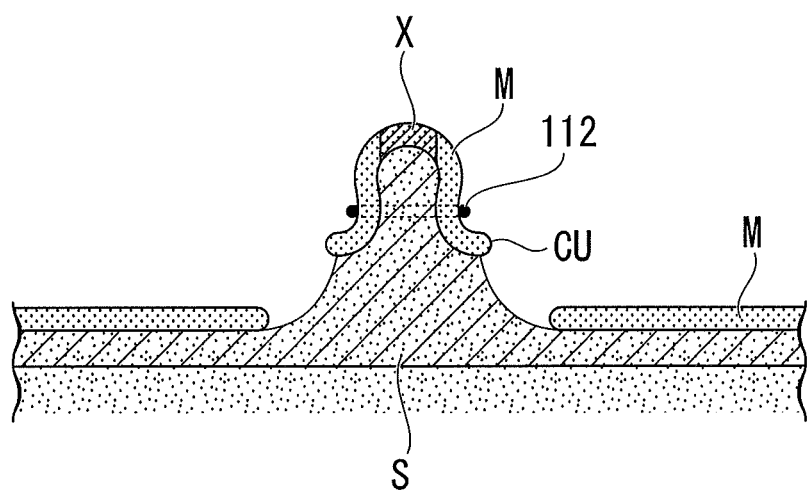
FIG. 35 is a view showing another endoscope procedure instrument, and the action thereof, according to FIG. 34.

As shown in FIGS. 34 and 35, it is also acceptable to make visual confirmation of the submucosa S via the endoscope easier by draping a constrictor 112, consisting of a ring-shaped elastic member such as rubber or a spring, around the cut opening CU of the mucosa M once the entire periphery of the mucosa M has been incised, and then tightening this constrictor 112 around the mucosa M.

Figure 36:
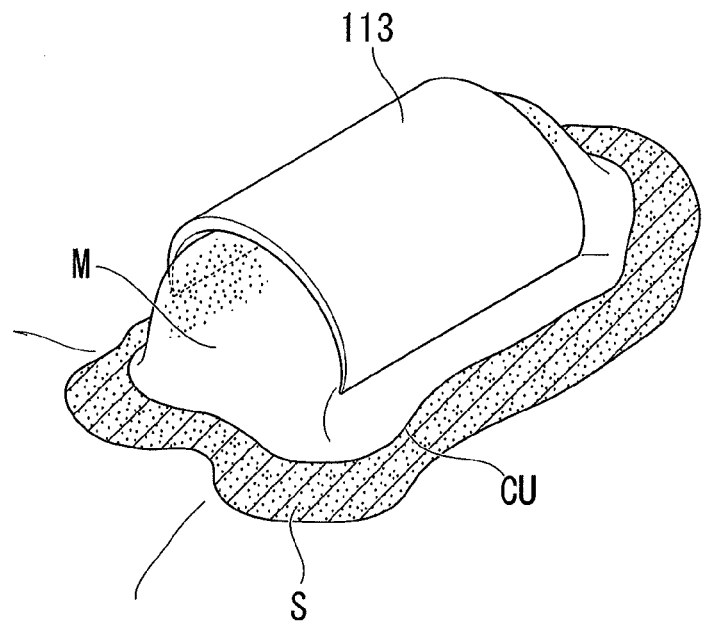
FIG. 36 is a view showing another endoscope procedure instrument, and the action thereof, in accordance with an ESD procedure.

Further, as shown in FIG. 36, a member in the form of a curved plate spring may be used as the constrictor 113. In this case, it is acceptable to provide for easier visual confirmation of the submucosa S via the endoscope by applying the ends of the constrictor 113 near the cut opening CU of the mucosa M, and then tightening this constictor 113 around the mucosa M.

Figure 37:
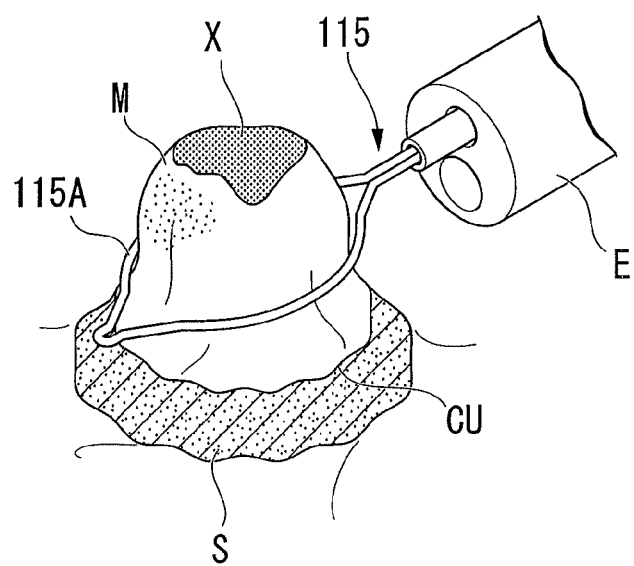
FIG. 37 is a view showing another endoscope procedure instrument, and the action thereof, in accordance with an ESD procedure.

In addition, as shown in FIG. 37, it is acceptable to provide for easier visual confirmation of the submucosa S via the endoscope by projecting a snare 115 out from the endoscope E, applying the snare wire 115A around the cut opening CU of the mucosa M, and then tightening this snare wire 115A around the mucosa M.

Figure 38:
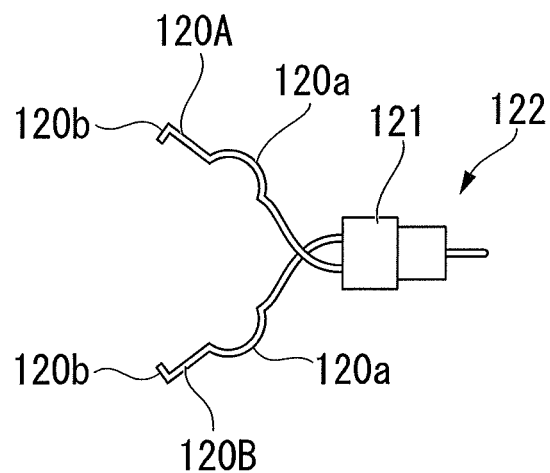
FIG. 38 is a view showing another endoscope procedure instrument in accordance with an ESD procedure.
Figure 39:
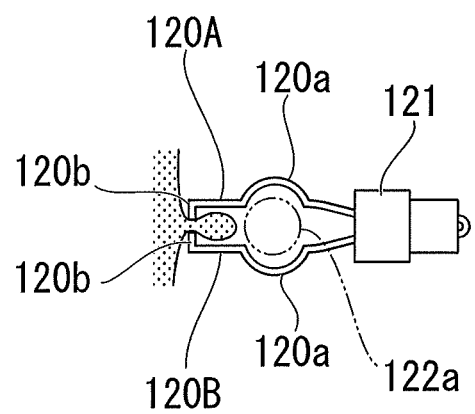
FIG. 39 is a view showing the action of another endoscope procedure instrument in accordance with an ESD procedure.

Another reference example is shown in FIGS. 38 through 41. In this reference example, as shown in FIG. 38, it is acceptable to employ a clip 122 that is provided with a pair of arms 120A,120B that are formed by bending a single strap; and a tube 121 that engages with the bottom part, not shown in the figures, of the pair of arms 120A,120B and is for closing the same. As shown in FIG. 39, a curved part 120*a* is formed to a part of each of the paired arms 120A,120B, and, when the paired arms 120A,120B are closed, these curve parts 120*a* form the insertion hole 122*a* into which procedure instruments such as gripping forceps, etc. can be inserted. Further, a claw 120*b* is provided to the front end of each of the paired arms 120A,120B.

An explanation will now be provided for the case where this clip 122 is employed in a procedure.

Figure 40:
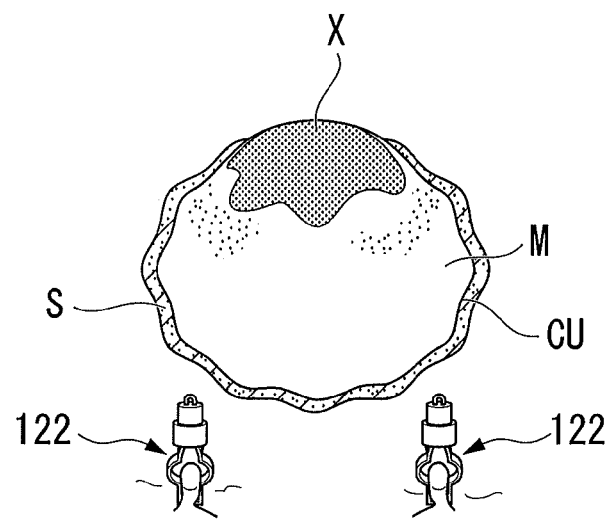
FIG. 40 is a view showing the action of another endoscope procedure instrument in accordance with an ESD procedure.
Figure 41:
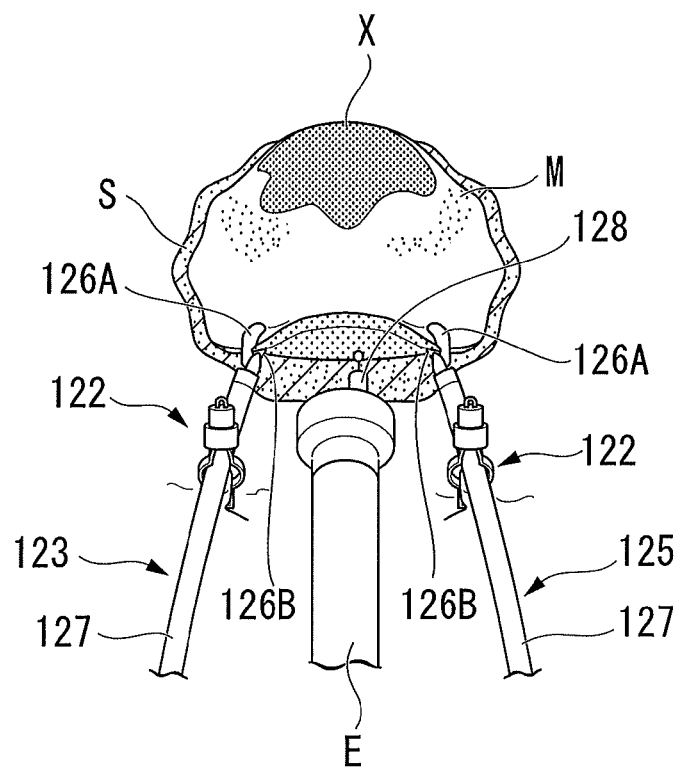
FIG. 41 is a view showing the action of another endoscope procedure instrument in accordance with an ESD procedure.

As shown in FIGS. 40 and 41, when the direction of insertion of the endoscope E is proximal side with respect to the entire circumferentially incised mucosa M, then the clips 122 are disposed at, for example, two different sites on the proximal side of the mucosa M that has not been cut so that the insertion holes 122*a* are opposite to the endoscope E. Gripping forceps 123,125 are inserted forward into the respective insertion holes 122*a*, and the cut mucosa M is gripped and lifted up by the pair of forceps pieces 126A,126B.

Here, gripping forceps 123,125 are inserted via the instrument insertion channel of the endoscope E in the case where the operator, not shown in the figures. can be released from the sheath 12, or, in the case where the operator cannot be released, are inserted into the instrument insertion channel of the endoscope E and then inserted through the insertion holes 122*a* of the clips 122. Once the forceps 123,125 have been inserted into the insertion hole 122*a*, it is preferable that the forceps pieces 126A,126B be energized in the open state so that they do not inadvertently become free from the insertion hole.

With the mucosa M elevated, a cutting tool such as a high-frequency blade 128 or the like is projected out from the endoscope E, to begin cutting of the submucosa S. Note that a different tool may be employed in place of clip 122, provided that it is one that can remain in the mucosa M. In this case, the insertion hole 122*a* is not limited to one that is formed by respective bending the pair of arms 120A,120B. Rather, it is also acceptable to provide an insertion hole 122*a* in which a wire or the like is formed into the shape of a loop.

In this clip 122, the forceps 123,125 can be supported near the diseased site, and the mucosa M can be elevated regardless of the motion of the endoscope E.

Figure 42:
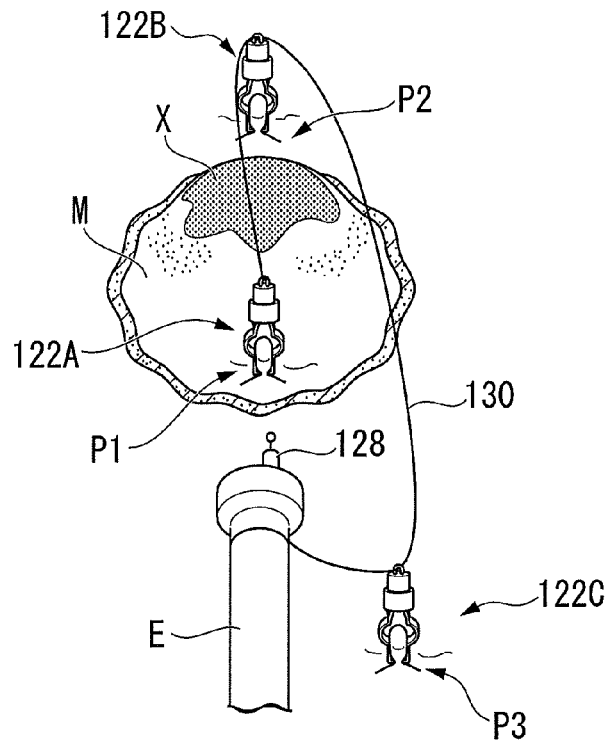
FIG. 42 is a view showing the action of another endoscope procedure instrument in accordance with an ESD procedure.
Figure 43:
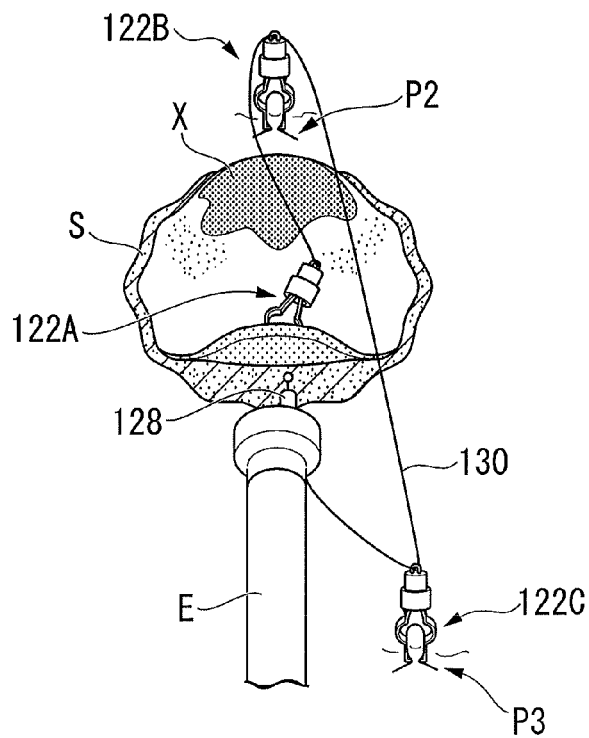
FIG. 43 is a view showing the action of another endoscope procedure instrument in accordance with an ESD procedure.
Figure 44:
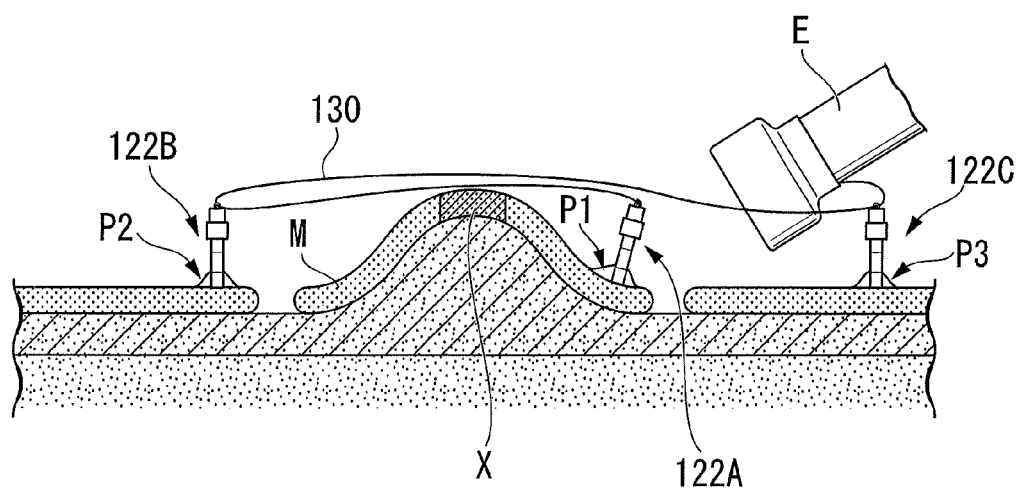
FIG. 44 is a view showing the action of another endoscope procedure instrument in accordance with an ESD procedure.

A different disposition for the clip is shown in FIGS. 42 through 44.

First, a first clip 122A is disposed to a position P1 which is the position on the cut side of the entirely circumferentially incised mucosa M which is closest to the endoscope E. A second clip 122B is disposed to a position P2 on the uncut side of the mucosa M adjacent to the position on the cut side of the mucosa M which is farthest from the endoscope E. A third clip 122C is disposed to an optional position P3 near the endoscope E. Suture 130, one end of which is connected to the first clip 122A is passed through the insertion holes 122*a* of the second clip 122B and the third clip 122C, and the other end is fixed to the endoscope E. Alternatively, the suture 130 may be disposed onto the mucosa M in advance, and then grasped by each of the clips 122A,122B,122C.

In the step for fixing the suture 130 to the endoscope E, it is acceptable, for example, to attach a cap with an externally attached tube, not shown in the figures, and then sequentially dispose the clips 122A,122B,122C from the externally attached tube. Then, with the suture 130 remaining inside the tube, it may be fixed in place by being gripped with gripping forceps, not shown in the figures.

Next, the suture 130 is pulled and moves accompanying the progression of the endoscope E toward the diseased site X, thereby lifting up the mucosa M. A cutting tool such as a high-frequency blade 128 or the like is then projected out from the endoscope E, and the submucosa S is cut.

With this clip 122A,122B,122C and the suture 130, the endoscope E can be supported near the diseased site X, and the mucosa M can be lifted up accompanying the advancing/retracting operation of the endoscope E.

In addition, the tube part may be provided as a component part of the endoscope, by being employed as the front end of the endoscope rather than as the refitting cap (endoscope procedure instrument).

In the present invention, a grasping member is provided to the outer peripheral surface of the tube part. As a result, when incising the submucosa, in the case where the tube part, attached to the endoscope, has been passed under the mucosa, it is possible to lift up the mucosa using the grasping member and to hold the mucosa so that the front surface of the submucosa can be visualized via the endoscope. Further, since the grasping member is disposed in the slit, the state of grasping by the grasping member can be visually confirmed from inside the tube part via the endoscope.

The present invention is provided with a grasping member. As a result, when incising the submucosa, in the case where the tube part, attached to the endoscope, has been passed under the mucosa, it is possible lift up the mucosa using the grasping member and to hold the mucosa so that the front surface of the submucosa can be visualized via the endoscope. Moreover, since a transfer member is provided, it is not necessary to regrip the mucosa, even as incising progresses. The transfer member can be used to move the grasping member to a position that facilitates the procedure and ensures a sufficient visual field. As a result, the procedure can be carried out more easily.

Because the grasping member is disposed within a slit in the present invention, it is possible to visually confirm the state of grasping by the grasping member from inside the tube part via the endoscope.

In the present invention, the grasping member can be freely moved toward the front end side or the base end side of the tube part. As a result, the grasping member can be moved to a more optimal position for carrying out the procedure.

By pulling the grasping member with respect to the tube part toward the proximal side, a rotational moment is generated at the front end side of the connector via the second rotational axis, and the front end side of the connector is lifted up with respect to the tube part, rotating about the first rotational axis.

By inflating the balloon, it is possible to elevate the grasping member in the vicinity of the second position with respect to the tube part, employing the first position as the point of support.

By advancing or retracting the operating member along the central axis of the tube part, the tongue piece can rotate about the position of pivot support with respect to the tube main body in the present invention.

In the present invention, the grasping member is provided with a pair of forceps. As a result, it is possible to grip the biological tissue with the pair of forceps by advancing/retracting manipulation of the operation wire with respect to the sheath.

In the present invention, the grasping member is provided with a pair of forceps. Accordingly, the biological tissue can be gripped with the pair of forceps by advancing and retracting manipulation of the operation wire with respect to the sheath. Further, since the grasping member is disposed inside a slit so as to permit visual confirmation via the endoscope, a procedure can be carried out while confirming the holding state of the biological tissue by the grasping member.

In the present invention, it is possible to grip the biological tissue with respect to the tube part by projecting the needle out from the front end of the tube member and piercing the biological tissue.

In the present invention, it is possible to grasp the biological tissue at the front end surface of the tube member by using the suction source to apply suction to the tube member.

The normal line of the front end surface of the tube member extends outward in the radial direction of the tube part in the present invention. As a result, it is possible to increase the area of contact between the front end surface and the biological tissue even more than in the case where the normal line of the front end surface is parallel with the central axis. Accordingly, it is possible to grasp the biological tissue with greater reliability.

By bringing the biological tissue into contact with the irregular portion, it is possible to generate a larger amount of frictional force than in the case of another surface which does not have an irregular portion, and, therefore, to grip the biological tissue with greater reliability against the tube part.

The present invention is provided with a procedure instrument. As a result, when incising the submucosa, in the case where the front end part of the endoscope has been introduced under the mucosa, the mucosa can be lifted up on the front end part of the procedure instrument, and be held so as to permit the front surface of the submucosa to be visualized from the endoscope. Further, the front end part of the procedure instrument can be moved by rotating the connector around the first rotational axis and the second rotational axis. Accordingly, it is not necessary to regrip the mucosa even as incising progresses. As a result, the front end part can be moved to a position that facilitates the procedure and ensures a sufficient visual field. Accordingly, the procedure can be carried out more easily.

In the present invention, once the tube part, attached to the endoscope, has been passed under the mucosa, the mucosa is lifted up on the procedure instrument and can be held so as to enable the front of the submucosa to be visualized via the endoscope.

In the present invention, the procedure instrument revolves by means of advancing/retracting manipulation with respect to the front end part of the endoscope. As a result, it is possible to more easily move the front end part of the procedure instrument toward or away from the front end part of the endoscope.

In the present invention, it is possible to incline the front end part of the procedure instrument in a direction that is perpendicular with respect to the front end part of the endoscope.

The present invention enables a decrease in the number of component parts.

Moreover, by means of the present invention, when incising the submucosa, it is possible to carry out the incising procedure while continuously maintaining an endoscopic field of view that is suitable for the procedure.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope procedure instrument comprising:
   a tube part formed in a cylindrical shape and projected in a longitudinal direction from a distal end of an endoscope, a proximal end of the tube part being connected to the distal end of the endoscope,
   a tongue piece rotatably disposed on the tube part, the tongue piece defining an outer surface and an interior in optical communication with the distal end of the endoscope;
   a grasping member configured to hold a biologic tissue, the grasping member being fixed to the outer surface of the tongue piece and projecting radially outward from the outer surface of the tongue piece; and
   an operation member connected to the tongue piece such that an articulation of the operation member rotates the tongue piece relative to the tube part.

2. The endoscope procedure instrument according to claim 1, wherein the grasping member comprises an irregular portion to hold a biologic tissue, the irregular portion being disposed on the outer surface of the tongue piece.

3. The endoscope procedure instrument according to claim 2, wherein the irregular portion comprises a plurality of projections.

4. The endoscope procedure instrument according to claim 1, further comprising a pivot for rotatably disposing the tongue piece relative to the tube part, wherein the grasping member is offset in the longitudinal direction from the pivot.

5. The endoscope procedure instrument according to claim 1, further comprising an external tube, the operation member being movably disposed in the external tube, the external tube being connected with an outer peripheral surface of the tube part.

6. An endoscope procedure instrument comprising:
   a tube part formed in a cylindrical shape and projected in a longitudinal direction from a distal end of an endoscope, a proximal end of the tube part being connected to the distal end of the endoscope,
   a tongue piece rotatably disposed on the tube part, at least a portion of the tongue piece extending distally from the distal end of the endoscope;
   a grasping member configured to hold a biologic tissue, the grasping member being fixed to the outer surface of the tongue piece and projecting from an outer surface of the tongue piece at the portion of the tongue piece; and
   an operation member connected to the tongue piece such that an articulation of the operation member rotates the tongue piece relative to the tube part.

7. The endoscope procedure instrument according to claim 6, wherein the grasping member comprises an irregular portion to hold a biologic tissue, the irregular portion being disposed on the portion of the tongue piece.

8. The endoscope procedure instrument according to claim 7, wherein the irregular portion comprises a plurality of projections.

9. The endoscope procedure instrument according to claim 6, further comprising a pivot for rotatably disposing the tongue piece relative to the tube part, wherein the grasping member is offset in the longitudinal direction from the pivot.

10. The endoscope procedure instrument according to claim 6, further comprising an external tube, the operation member being movably disposed in the external tube, the external tube being connected with an outer peripheral surface of the tube part.

* * * * *